(12) United States Patent
Neumann

(10) Patent No.: US 11,250,337 B2
(45) Date of Patent: Feb. 15, 2022

(54) SYSTEMS AND METHODS FOR CLASSIFYING MEDIA ACCORDING TO USER NEGATIVE PROPENSITIES

(71) Applicant: Kenneth Neumann, Lakewood, CO (US)

(72) Inventor: Kenneth Neumann, Lakewood, CO (US)

(73) Assignee: KPN INNOVATIONS LLC, Lakewood, CO (US)

( * ) Notice: Subject to any disclaimer, the term of this patent is extended or adjusted under 35 U.S.C. 154(b) by 0 days.

(21) Appl. No.: 16/673,673

(22) Filed: Nov. 4, 2019

(65) Prior Publication Data

US 2021/0133604 A1 May 6, 2021

(51) Int. Cl.
*G06N 5/04* (2006.01)
*G06N 20/00* (2019.01)
*G06F 16/28* (2019.01)

(52) U.S. Cl.
CPC ............ *G06N 5/04* (2013.01); *G06F 16/285* (2019.01); *G06N 20/00* (2019.01)

(58) Field of Classification Search
CPC ......... G06N 5/04; G06N 20/00; G06F 16/285
See application file for complete search history.

(56) References Cited

U.S. PATENT DOCUMENTS

| | | | |
|---|---|---|---|
| 5,645,986 A | 7/1997 | West et al. | |
| 9,169,516 B2 | 10/2015 | Cawthon | |
| 9,185,238 B1 | 11/2015 | Freeland et al. | |
| 9,600,297 B1 | 3/2017 | Buyukkokten | |
| 9,948,689 B2 | 4/2018 | Savage et al. | |
| 9,965,553 B2 | 5/2018 | Lyren | |
| 10,087,486 B2 | 10/2018 | Zhang et al. | |
| 10,168,866 B2 | 1/2019 | Wakeen | |
| 10,316,366 B2 | 6/2019 | Harley et al. | |
| 2003/0082597 A1 | 5/2003 | Cannon et al. | |

(Continued)

OTHER PUBLICATIONS

Provencal et al, Differential DNA Methylation Regions in Cytokine and Transcription Factor Genomic Loci Associate with Childhood Physical Aggression, 2013, PLoS One (Year: 2013).*

(Continued)

*Primary Examiner* — Kevin W Figueroa
(74) *Attorney, Agent, or Firm* — Caldwell Intellectual Property Law, LLC

(57) ABSTRACT

A system for classifying media according to user negative propensities, includes a computing device configured to identify a negative behavioral propensity associated with a human subject, generate, using a classification algorithm, a media theme classifier, wherein the media theme classifier inputs media items and outputs principal themes of the media items, receive a media item to be transmitted to a device operated by the human subject, identify, using the media theme classifier, a principal theme of the media item, and determine if the principle theme matches the negative behavioral propensity. Identifying the principal theme further includes extracting, from the media item, a plurality of media item content elements, classifying each content element of the plurality of media item content elements to a media item object of a plurality of media item objects using an object classifier, and inputting the plurality of objects to the media theme classifier.

20 Claims, 5 Drawing Sheets

(56) References Cited

U.S. PATENT DOCUMENTS

| | | |
|---|---|---|
| 2003/0157526 A1 | 8/2003 | Weindruch et al. |
| 2009/0048903 A1 | 2/2009 | Lieberman |
| 2009/0307180 A1 | 12/2009 | Colby et al. |
| 2014/0063236 A1* | 3/2014 | Shreve ............... G06K 9/00228 348/143 |
| 2014/0088995 A1 | 3/2014 | Damani |
| 2014/0274767 A1* | 9/2014 | Yegnasubramanian ..................... C12Q 1/6855 506/9 |
| 2014/0276244 A1 | 9/2014 | Kamyar |
| 2014/0310019 A1 | 10/2014 | Blander et al. |
| 2016/0117595 A1* | 4/2016 | Zhang ................... G06Q 10/10 706/12 |
| 2016/0162785 A1 | 6/2016 | Grobman |
| 2016/0212076 A1 | 7/2016 | Bellissimo et al. |
| 2016/0314265 A1 | 10/2016 | Sternberg et al. |
| 2017/0116386 A1 | 4/2017 | Shu |
| 2017/0235849 A1 | 8/2017 | Jacob |
| 2017/0286625 A1 | 10/2017 | Blander et al. |
| 2018/0176727 A1* | 6/2018 | Williams ............... A61B 5/747 |
| 2018/0205704 A1* | 7/2018 | Terry ................. H04L 63/0245 |
| 2019/0027052 A1 | 1/2019 | Moore |
| 2019/0095716 A1* | 3/2019 | Shrestha ............. G08B 21/187 |
| 2019/0106747 A1 | 4/2019 | Niculescu, III et al. |
| 2019/0125239 A1* | 5/2019 | Lyoo .................. A61B 5/02405 |
| 2020/0035222 A1* | 1/2020 | Sypniewski ............ G10L 15/02 |

OTHER PUBLICATIONS

Tremblay RE, Nagin DS, Séguin JR, et al. Physical aggression during early childhood: trajectories and predictors. Pediatrics. 2004; 114(1):e43-e50. doi:10.1542/peds.114.1.e43 (Year: 2004).*

Shalev et al.; Stress and Telomere Biology: A lifespan perspective; Psychoneuroendocrinology 38, No. 9: 1835-1842; https://www.ncbi.nlm.nih.gov/pmc/articles/PMC3735679/pdf/nihms-457197.pdf; Sep. 1, 2013.

Jia et al.; Common methods of biological age estimation; Clinical interventions in aging 12: 759; https://www.ncbi.nlm.nih.gov/pmc/articles/PMC5436771/pdf/cia-12-759.pdf; May 11, 2017.

Enroth et al; Protein profiling reveals consequences of lifestyle choices on predicted biological aging; Scientific reports 5: 17282; https://www.nature.com/articles/srep17282.pdf; Dec. 1, 2015.

Zhang et al.; Select aging biomarkers based on telomere length and chronological age to build a biological age equation; Age 36, No. 3: 9639; https://www.ncbi.nlm.nih.gov/pmc/articles/PMC4082565/pdf/11357_2014_Article_9639.pdf; Jun. 1, 2014.

Online spiritual advisor services; http://www.askforadvisors.com/psychic-readings/index.php; Apr. 22, 2019.

24 Astro Spiritual Advisor; https://play.google.com/store/apps/details?id=infrasat.astro24; Feb. 18, 2019.

Chatnow; https://chatnow.org/; Apr. 22, 2019.

PCT/US2020/039115, International Search Report, dated Jul. 23, 2020.

* cited by examiner

SYSTEMS AND METHODS FOR CLASSIFYING MEDIA ACCORDING TO USER NEGATIVE PROPENSITIES

FIELD OF THE INVENTION

The present invention generally relates to the field of artificial intelligence. In particular, the present invention is directed to systems and methods for classifying media according to user negative propensities.

BACKGROUND

It is axiomatic that media will be created for the purpose of engaging the interest of its purveyors by appealing to their aesthetic or physical appetites and proclivities. While this may be harmless as a general matter, for those with latent or habitual susceptibility to temptation, such machinations may have disastrous consequences. Prediction of such impacts, given the multiplicity of channels and creators, has thus far presented insurmountable challenges of data complexity.

SUMMARY OF THE DISCLOSURE

In an aspect, a system for classifying media according to user negative propensities includes a computing device configured to identify a negative behavioral propensity associated with a human subject, generate, using thematic training data including a plurality of media items and a plurality of correlated themes, and using a classification algorithm, a media theme classifier, wherein the media theme classifier inputs media items and outputs principal themes of the media items, receive a media item to be transmitted to a device operated by the human subject, identify, using the media theme classifier, a principal theme of the media item, and determine if the principle theme matches the negative behavioral propensity. Identifying the principal theme further comprises extracting, from the media item, a plurality of media item content elements, classifying each content element of the plurality of media item content elements to a media item object of a plurality of media item objects using an object classifier, and inputting the plurality of objects to the media theme classifier.

In another aspect, a method of classifying media according to user negative propensities includes identifying a negative behavioral propensity associated with a human subject. The method includes generating, by the computing device and using thematic training data including a plurality of media items and a plurality of correlated themes, and using a classification algorithm, a media theme classifier, wherein the media theme classifier inputs media items and outputs principal themes of the media items. The method includes receiving, by the computing device, a media item to be transmitted to a device operated by the human subject. The method includes identifying, by the computing device and using the media theme classifier, a principal theme of the media item, wherein identifying the principal theme further includes extracting, from the media item, a plurality of media item content elements, classifying each content element of the plurality of media item content elements to a media item object of a plurality of media item objects using an object classifier, and inputting the plurality of objects to the media theme classifier. The method includes determining, by the computing device, if the principle theme matches the negative behavioral propensity.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, embodiments disclosed herein automatically detect a human subject's propensity to problematic behaviors such as addictions using feature learning regarding biological extractions. Such propensities may be used to avoid exposure of a human subject to media representing a moral hazard given propensities and/or past behavior.

Figure 1:
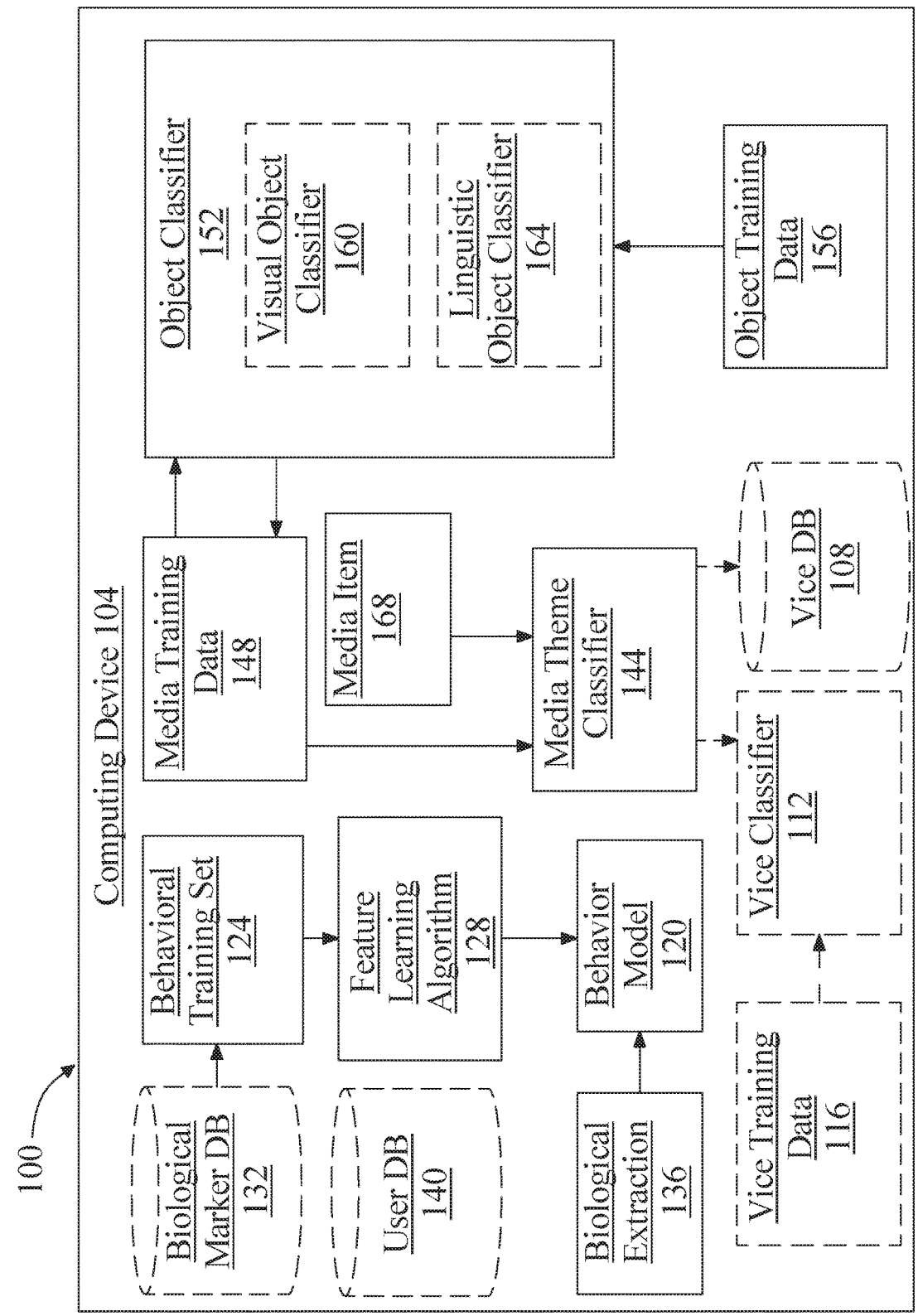
FIG. 1 is a block diagram illustrating an exemplary embodiment of a system for classifying media according to user negative propensities.

Referring now to FIG. 1, an exemplary embodiment of a system 100 for classifying media according to user negative propensities is illustrated. System 100 includes a computing device 104. Computing device 104 may include any computing device 104 as described in this disclosure, including without limitation a microcontroller, microprocessor, digital signal processor (DSP) and/or system on a chip (SoC) as described in this disclosure. Computing device 104 may include, be included in, and/or communicate with a mobile device such as a mobile telephone or smartphone. Computing device 104 may include a single computing device 104 operating independently or may include two or more computing device 104 operating in concert, in parallel, sequentially or the like; two or more computing devices 104 may be included together in a single computing device 104 or in two or more computing devices 104. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices 104, and any combinations thereof. A network may employ a wired and/or a wireless mode of communication. In general, any network topology may be used. Information (e.g., data, software etc.) may be communicated to and/or from a computer and/or a computing device 104. Computing device 104 may include but is not limited to, for example, a computing device 104 or cluster of computing devices 104 in a first location and a second computing device 104 or cluster of computing devices 104 in a second location. Computing device 104 may include one or more computing devices 104 dedicated to data storage, security, distribution of traffic for load balancing, and the like. Computing device 104 may distribute one or more computing tasks as described below across a plurality of computing devices 104 of computing device 104, which may operate in parallel, in series, redundantly, or in any other manner used for distribution of tasks or memory between computing devices 104. Computing device 104 may be implemented using a "shared nothing" architecture in which data is cached at the worker; in an embodiment, this may enable scalability of system 100 and/or computing device 104.

Still referring to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Continuing to refer to FIG. 1, computing device 104 may be designed and configured to identify a negative behavioral propensity associated with a human subject. A "negative behavioral propensity," as used in this disclosure, is an elevated risk of developing a negative behavior, where a "negative behavior," also referred to herein as a "problematic behavior," is defined as an addictive or self-injurious behavior. A negative behavior may include, without limitation, an addition to a chemical substance, such as an addiction to narcotics, stimulants such as cocaine, cocaine derivatives, amphetamines, methamphetamine, nicotine, or the like, opiates such as heroine, fentanyl, oxycodone, or the like, *cannabis, cannabis*-derived compounds such as THC, depressants such as alcohol, barbiturates, benzodiazepines, or the like, MDMA, PCP, hallucinogens such as LSD, addictions to any of various prescription drugs, or the like. As a further non-limiting example, a negative behavior may include an addition to an act, such as a gambling addition, a sex addiction characterized by compulsive engagement in sexual activity, a pornography addiction characterized by compulsive sexual activity concurrent with pornography consumption, gaming disorder characterized by compulsive use of Internet or video games, gambling addiction and/or problem gambling as characterized by compulsive or continuous gambling despite resulting financial harm, food addiction as characterized by compulsive overeating, an eating disorder such as anorexia or bulimia, or the like.

Still referring to FIG. 1, remote device may include a device operated by human subject; for instance, human subject may provide the input after a lapse in self-control. Alternatively or additionally, another person, potentially from a different remote device, may report that human subject has engaged in the problematic behavior. For instance, a family member, neighbor, spouse, boyfriend, girlfriend, ex-boyfriend, ex-girlfriend, religious leader, co-worker, or the like may observe human subject engaging in problematic behavior, such as a drinking binge, a visit to an adult entertainment institution, an excessive shopping spree, weekend at a casino, a hit of an addictive drug, or the like. Computing device 104 may track such notifications and/or compare such notifications to negative behavioral propensities. For instance, computing device 104 may record a first such report as indicative that human subject is at an elevated risk to engage in problematic behavior. In an embodiment, one or more words and/or phrases entered by a user, who may include any user as described above, may be mapped to a label, or particular word or phrase used by computing device 104 to describe an object, behavior, problematic behavior, negative behavioral tendency, or the like, using a language processing model, module, and/or algorithm as described below; for instance, computing device 104 may determine using a language processing model, module, and/or algorithm as described below that the word or phrase entered by the user is a synonym of the label, and may substitute the label for the word or phrase. User entries may alternatively or additionally include a media item, as defined in further detail below, such as a media item a user reports to have been watched, listened to, or otherwise consumed by human subject; media item may, without limitation, be associated with objects contained therein using object classifiers as described in further detail below, outputs of which computing device 104 may treat in a like manner to user-input words, phrases, and/or identifications.

With continued reference to FIG. 1, user entry may directly identify a problematic behavior and/or negative behavioral propensity, for instance by selection from a list thereof displayed on a remote device operated by user. Alternatively or additionally, computing device 104 may identify negative behavior by querying a vice database 108 using user-entered data. In an embodiment, vice database 108 may include any data structure for ordered storage and retrieval of data, which may be implemented as a hardware or software module. Vice database 108 may be implemented, without limitation, as a relational database, a key-value retrieval datastore such as a NOSQL database, or any other format or structure for use as a datastore that a person skilled in the art would recognize as suitable upon review of the entirety of this disclosure. Data entries in a vice database 108 may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a vice database 108 may reflect categories, cohorts, and/or populations of data consistently with this disclosure.

Still referring to FIG. 1, vice database 108 may be populated with one or more relationships between labels, objects, themes, or the like, as introduced in further detail below, and problematic behaviors and/or negative behavioral propensities; such relationships may be entered in vice database 108 by users, where user entry may include entry by one or more expert users such as psychologists, medical experts, or the like, "crowd-sourced" entry by large numbers of users, which may be aggregated, or the like. Where user entries are aggregated, aggregated results may include comparison of aggregated values to threshold numbers; for instance, a relationship between a given label and a problematic behavior and/or negative behavioral propensity may be recorded where more than a threshold percentage of user entries have identified the two as linked. Relationships between labels, objects, themes, or the like, as introduced in further detail below, and problematic behaviors and/or negative behavioral propensities may alternatively or additionally be entered by computing device from a vice classifier as described below; for instance a label may be entered in vice database 108 with a problematic behavior and/or negative behavioral propensity most probably associated therewith as identified by a vice classifier.

Alternatively or additionally, and still referring to FIG. 1, computing device 104 may input user inputs to a vice classifier 112, and receive an output classifying user inputs to one or more problematic behaviors and/or negative behavioral propensities. Computing device 104 may generate vice classifier 112 using a classification algorithm, defined as a processes whereby a computing device 104 derives, from training data, a model known as a "classifier" for sorting inputs into categories or bins of data. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

With continued reference to FIG. 1, training data, as used in this disclosure, is data containing correlations that a machine-learning process may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine-learning processes as described in further detail below. Training data may be formatted and/or organized by categories of data elements, for instance by associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements; for instance, and without limitation, training data may be provided in fixed-length formats, formats linking positions of data to categories such as comma-separated value (CSV) formats and/or self-describing formats such as extensible markup language (XML), enabling processes or devices to detect categories of data.

Alternatively or additionally, and still referring to FIG. 1, training data may include one or more elements that are not categorized; that is, training data may not be formatted or contain descriptors for some elements of data. Machine-learning algorithms and/or other processes may sort training data according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data to be made applicable for two or more distinct machine-learning algorithms as described in further detail below. Training data used by computing device 104 may correlate any input data as described in this disclosure to any output data as described in this disclosure.

Still referring to FIG. 1, vice training data 116, used herein as training data used to generate vice classifier 112, may include, without limitation, a plurality of data entries, each data entry including one or more themes and/or objects and one or more negative behavioral propensities and/or negative behaviors represented thereby and/or associated therewith. Vice training data 116 and/or elements thereof may be entered by users, for instance via graphical user interface forms; as a non-limiting example, each such form may present to a user a geometric form, word, image, or the like, and a user may select a label of a negative behavior and/or negative behavioral propensity for each such geometric form, word, image, or the like from a list of labels provided to the user and/or may enter one or more words in a text entry element, which may be mapped to labels using language processing as described below. As a non-limiting example, a user may be provided with a beer commercial, and "tag" or identify one or more images and or words in the beer commercial as associated with alcoholism, such as glasses, cans, and/or bottles of beer, a bar, a brand name of a well-known beer, a voiceover mentioning the beer brand, the word beer, or making one or more statements extolling the beer brand or drinking generally; a user may further label an attractive person dressing and/or behaving in a sexually suggestive manner as relating to sex addiction or pornography addiction. As a further example a user viewing an advertisement for a casino may flag or tag various objects therein as relating to various negative behavioral propensities and/or negative behaviors, such as without limitation flagging depictions of cocktails as associated with alcoholism, flagging depictions of sexually suggestive behavior, attire, or persons as associated with sex addiction or pornographic addiction, flagging depictions of food consumption as associated with food addictions or eating disorders, flagging depictions of shopping sprees, shopping bags, or designer clothes with compulsive shopping, flagging depictions of gambling devices, paraphernalia, dice, cards, blackjack tables, gambling chips, slot machines, or the like with gambling addictions, and so forth.

Still referring to FIG. 1, computing device 104 may be configured to generate vice classifier 112 using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A) P(A) \div P(B)$, where P(AB) is the probability of hypothesis A given data B also known as posterior probability; P(B/A) is the probability of data B given that the hypothesis A was true; P(A) is the probability of hypothesis A being true regardless of data also known as prior probability of A; and P(B) is the probability of the data regardless of the hypothesis. A naïve Bayes algorithm may be generated by first transforming training data into a frequency table. Computing device 104 may then calculate a likelihood table by calculating probabilities of different data entries and classification labels. Computing device 104 may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 1, computing device 104 may be configured to generate vice classifier 112 using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 1, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm: $l=\sqrt{\sum_{i=0}^{n} a_i^2}$, where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values. As a non-limiting example, K-nearest neighbors algorithm may be configured to classify an input vector including a plurality of user-entered words and/or phrases, a plurality of attributes of a media item, such as spoken or written text, objects depicted in images, metadata, or the like, to clusters representing themes.

Vice classifier 112 may relate themes and/or objects to clusters corresponding to labels of negative behaviors and/or negative behavior propensities. Where vice classifier 112 is updated, for instance by adding to a list of negative behavioral propensities and/or negative behaviors corresponding to clusters and rerunning vice classifier 112 to classify to the updated list, principal themes and/or objects stored in memory may be subjected to vice classifier 112 again to update association of principal themes and/or objects with negative behaviors and/or negative behavioral propensities;

each of these actions, including without limitation rerunning vice classifier 112 to classify to the updated list and/or updating plurality of negative behavioral propensities and/or negative behaviors, may be performed by computing device 104. Vice classifier 112 may be run against one or more sets of vice training data 116, where vice training data 116 may include any form of training data as described above.

Still referring to FIG. 1, vice classifier 112 may alternatively or additionally be customized to human subject. For instance, and without limitation, a vice classifier 112 create using vice training data 116 as described above may be modified using augmented or updated training data matching negative behavioral propensities and/or negative behaviors to particular proclivities of human subject. For instance, and for the purposes of illustration only, if human subject has a media-related addiction such as a pornographic addiction, vice training data 116 may be generated to associate images, words, or other content elements related to human subject's particular focus of obsession with the negative behavior and/or negative behavioral propensity; such content elements may, for instance represent particular items of clothing, body parts, or the like, which while potentially innocuous for other users may act to inflame the lusts of human subject if encountered. Elements of vice training data 116 that correspond to such person-specific proclivities may be received from users, including human subject and/or other persons such as family members, friends, purveyors of content, spouses and/or "significant others" of human subject, ex-spouses, ex-boyfriends, ex-girlfriends, religious and/or psychological advisors, or the like. Alternatively or additionally, an object classifier as described below may be used to identify relative frequency of appearance of particular visual and/or textual elements in media consumed by human subject; for instance, a visual object classifier, as described in further detail below, may be run against a series of media selections by the user may identify one or more visual and/or textual objects that appear related to the user's media-related additions, such as. System may match such items to problematic behavior via a user-modified vice-classifier for instance by adding clusters and/or labels to a general vice classifier 112 and/or by adding such items to a vice database 108. As a result, such elements may also be identified, via database lookup and/or vice classifier 112, as matching problematic behavior. For instance, where a particular article of clothing and/or footwear matches a media-based addiction for human subject, advertisements for such clothing and/or footwear may be blocked, as well as advertisements prominently displaying and/or using such clothing and/or footwear.

With continued reference to FIG. 1 computing device 104 may be designed and configured to identify negative behavioral propensity using a behavior model 120 correlating physiological state data with negative behavioral propensities. As used in this disclosure, "physiological state data" is any data indicative of a person's physiological state; physiological state may be evaluated with regard to one or more measures of health of a person's body, one or more systems within a person's body such as a circulatory system, a digestive system, a nervous system, or the like, one or more organs within a person's body, and/or any other subdivision of a person's body useful for diagnostic or prognostic purposes. For instance, and without limitation, a particular set of biomarkers, test results, and/or biochemical information may be recognized in a given medical field as useful for identifying various disease conditions or prognoses within a relevant field. As a non-limiting example, and without limitation, physiological data describing red blood cells, such as red blood cell count, hemoglobin levels, hematocrit, mean corpuscular volume, mean corpuscular hemoglobin, and/or mean corpuscular hemoglobin concentration may be recognized as useful for identifying various conditions such as dehydration, high testosterone, nutrient deficiencies, kidney dysfunction, chronic inflammation, anemia, and/or blood loss.

Physiological state data may include, without limitation, hematological data, such as red blood cell count, which may include a total number of red blood cells in a person's blood and/or in a blood sample, hemoglobin levels, hematocrit representing a percentage of blood in a person and/or sample that is composed of red blood cells, mean corpuscular volume, which may be an estimate of the average red blood cell size, mean corpuscular hemoglobin, which may measure average weight of hemoglobin per red blood cell, mean corpuscular hemoglobin concentration, which may measure an average concentration of hemoglobin in red blood cells, platelet count, mean platelet volume which may measure the average size of platelets, red blood cell distribution width, which measures variation in red blood cell size, absolute neutrophils, which measures the number of neutrophil white blood cells, absolute quantities of lymphocytes such as B-cells, T-cells, Natural Killer Cells, and the like, absolute numbers of monocytes including macrophage precursors, absolute numbers of eosinophils, and/or absolute counts of basophils. Physiological state data may include, without limitation, immune function data such as Interleukine-6 (IL-6), TNF-alpha, systemic inflammatory cytokines, and the like.

Continuing to refer to FIG. 1, physiological state data may include, without limitation, data describing blood-born lipids, including total cholesterol levels, high-density lipoprotein (HDL) cholesterol levels, low-density lipoprotein (LDL) cholesterol levels, very low-density lipoprotein (VLDL) cholesterol levels, levels of triglycerides, and/or any other quantity of any blood-born lipid or lipid-containing substance. Physiological state data may include measures of glucose metabolism such as fasting glucose levels and/or hemoglobin A1-C(HbA1c) levels. Physiological state data may include, without limitation, one or more measures associated with endocrine function, such as without limitation, quantities of dehydroepiandrosterone (DHEAS), DHEA-Sulfate, quantities of cortisol, ratio of DHEAS to cortisol, quantities of testosterone quantities of estrogen, quantities of growth hormone (GH), insulin-like growth factor 1 (IGF-1), quantities of adipokines such as adiponectin, leptin, and/or ghrelin, quantities of somatostatin, progesterone, or the like. Physiological state data may include measures of estimated glomerular filtration rate (eGFR). Physiological state data may include quantities of C-reactive protein, estradiol, ferritin, folate, homocysteine, prostate-specific Ag, thyroid-stimulating hormone, vitamin D, 25 hydroxy, blood urea nitrogen, creatinine, sodium, potassium, chloride, carbon dioxide, uric acid, albumin, globulin, calcium, phosphorus, alkaline photophatase, alanine amino transferase, aspartate amino transferase, lactate dehydrogenase (LDH), bilirubin, gamma-glutamyl transferase (GGT), iron, and/or total iron binding capacity (TIBC), or the like. Physiological state data may include antinuclear antibody levels. Physiological state data may include aluminum levels. Physiological state data may include arsenic levels. Physiological state data may include levels of fibronigen, plasma cystatin C, and/or brain natriuretic peptide.

Continuing to refer to FIG. 1, physiological state data may include measures of lung function such as forced expiratory volume, one second (FEV-1) which measures how much air can be exhaled in one second following a deep inhalation, forced vital capacity (FVC), which measures the volume of air that may be contained in the lungs. Physiological state data may include a measurement blood pressure, including without limitation systolic and diastolic blood pressure. Physiological state data may include a measure of waist circumference. Physiological state data may include body mass index (BMI). Physiological state data may include one or more measures of bone mass and/or density such as dual-energy x-ray absorptiometry. Physiological state data may include one or more measures of muscle mass. Physiological state data may include one or more measures of physical capability such as without limitation measures of grip strength, evaluations of standing balance, evaluations of gait speed, pegboard tests, timed up and go tests, and/or chair rising tests.

Still viewing FIG. 1, physiological state data may include one or more measures of cognitive function, including without limitation Rey auditory verbal learning test results, California verbal learning test results, NIH toolbox picture sequence memory test, Digital symbol coding evaluations, and/or Verbal fluency evaluations. Physiological state data may include one or more evaluations of sensory ability, including measures of audition, vision, olfaction, gustation, vestibular function and pain.

Continuing to refer to FIG. 1, physiological state data may include psychological data. Psychological data may include any data generated using psychological, neuro-psychological, and/or cognitive evaluations, as well as diagnostic screening tests, personality tests, personal compatibility tests, or the like; such data may include, without limitation, numerical score data entered by an evaluating professional and/or by a subject performing a self-test such as a computerized questionnaire. Psychological data may include textual, video, or image data describing testing, analysis, and/or conclusions entered by a medical professional such as without limitation a psychologist, psychiatrist, psychotherapist, social worker, a medical doctor, or the like. Psychological data may include data gathered from user interactions with persons, documents, and/or computing devices; for instance, user patterns of purchases, including electronic purchases, communication such as via chat-rooms or the like, any textual, image, video, and/or data produced by the subject, any textual image, video and/or other data depicting and/or describing the subject, or the like. Any psychological data and/or data used to generate psychological data may be analyzed using machine-learning and/or language processing modules as described in this disclosure.

Still referring to FIG. 1, physiological state data may include genomic data, including deoxyribonucleic acid (DNA) samples and/or sequences, such as without limitation DNA sequences contained in one or more chromosomes in human cells. Genomic data may include, without limitation, ribonucleic acid (RNA) samples and/or sequences, such as samples and/or sequences of messenger RNA (mRNA) or the like taken from human cells. Genetic data may include telomere lengths. Genomic data may include epigenetic data including data describing one or more states of methylation of genetic material. Physiological state data may include proteomic data, which as used herein is data describing all proteins produced and/or modified by an organism, colony of organisms, or system of organisms, and/or a subset thereof. Physiological state data may include data concerning a microbiome of a person, which as used herein includes any data describing any microorganism and/or combination of microorganisms living on or within a person, including without limitation biomarkers, genomic data, proteomic data, and/or any other metabolic or biochemical data useful for analysis of the effect of such microorganisms on other physiological state data of a person, and/or on prognostic labels and/or ameliorative processes as described in further detail below.

With continuing reference to FIG. 1, physiological state data may include one or more user-entered descriptions of a person's physiological state. One or more user-entered descriptions may include, without limitation, user descriptions of symptoms, which may include without limitation current or past physical, psychological, perceptual, and/or neurological symptoms, user descriptions of current or past physical, emotional, and/or psychological problems and/or concerns, user descriptions of past or current treatments, including therapies, nutritional regimens, exercise regimens, pharmaceuticals or the like, or any other user-entered data that a user may provide to a medical professional when seeking treatment and/or evaluation, and/or in response to medical intake papers, questionnaires, questions from medical professionals, or the like. Physiological state data may include any physiological state data, as described above, describing any multicellular organism living in or on a person including any parasitic and/or symbiotic organisms living in or on the persons; non-limiting examples may include mites, nematodes, flatworms, or the like. Examples of physiological state data described in this disclosure are presented for illustrative purposes only and are not meant to be exhaustive. Persons skilled in the art, upon reviewing the entirety of this disclosure, will be aware of various additional examples of physiological state data that may be used consistently with descriptions of systems and methods as provided in this disclosure.

With continued reference to FIG. 1, physiological data may be obtained from a physical sample. A "physical sample" as used in this example, may include any sample obtained from a human body of a user. A physical sample may be obtained from a bodily fluid and/or tissue analysis such as a blood sample, tissue, sample, buccal swab, mucous sample, stool sample, hair sample, fingernail sample and the like. A physical sample may be obtained from a device in contact with a human body of a user such as a microchip embedded in a user's skin, a sensor in contact with a user's skin, a sensor located on a user's tooth, and the like. Physiological data may be obtained from a physically extracted sample.

Continuing to refer to FIG. 1, user biological marker 112 contains a plurality of user body measurements. A "user body measurement" as used in this disclosure, includes a measurable indicator of the severity, absence, and/or presence of a disease state. A "disease state" as used in this disclosure, includes any harmful deviation from the normal structural and/or function state of a human being. A disease state may include any medical condition and may be associated with specific symptoms and signs. A disease state may be classified into different types including infectious diseases, deficiency diseases, hereditary diseases, and/or physiological diseases. For instance and without limitation, internal dysfunction of the immune system may produce a variety of different diseases including immunodeficiency, hypersensitivity, allergies, and/or autoimmune disorders.

With continued reference to FIG. 1, user body measurements may be related to particular dimensions of the human body. A "dimension of the human body" as used in this disclosure, includes one or more functional body systems that are impaired by disease in a human body and/or animal body. Functional body systems may include one or more body systems recognized as attributing to root causes of disease by functional medicine practitioners and experts. A "root cause" as used in this disclosure, includes any chain of causation describing underlying reasons for a particular disease state and/or medical condition instead of focusing solely on symptomatology reversal. Root cause may include chains of causation developed by functional medicine practices that may focus on disease causation and reversal. For instance and without limitation, a medical condition such as diabetes may include a chain of causation that does not include solely impaired sugar metabolism but that also includes impaired hormone systems including insulin resistance, high cortisol, less than optimal thyroid production, and low sex hormones. Diabetes may include further chains of causation that include inflammation, poor diet, delayed food allergies, leaky gut, oxidative stress, damage to cell membranes, and dysbiosis. Dimensions of the human body may include but are not limited to epigenetics, gut-wall, microbiome, nutrients, genetics, and/or metabolism.

With continued reference to FIG. 1, epigenetic, as used herein, includes any user body measurements describing changes to a genome that do not involve corresponding changes in nucleotide sequence. Epigenetic body measurement may include data describing any heritable phenotypic. Phenotype, as used herein, include any observable trait of a user including morphology, physical form, and structure. Phenotype may include a user's biochemical and physiological properties, behavior, and products of behavior. Behavioral phenotypes may include cognitive, personality, and behavior patterns. This may include effects on cellular and physiological phenotypic traits that may occur due to external or environmental factors. For example, DNA methylation and histone modification may alter phenotypic expression of genes without altering underlying DNA sequence. Epigenetic body measurements may include data describing one or more states of methylation of genetic material.

With continued reference to FIG. 1, gut-wall, as used herein, includes the space surrounding the lumen of the gastrointestinal tract that is composed of four layers including the mucosa, submucosa, muscular layer, and serosa. The mucosa contains the gut epithelium that is composed of goblet cells that function to secrete mucus, which aids in lubricating the passage of food throughout the digestive tract. The goblet cells also aid in protecting the intestinal wall from destruction by digestive enzymes. The mucosa includes villi or folds of the mucosa located in the small intestine that increase the surface area of the intestine. The villi contain a lacteal, that is a vessel connected to the lymph system that aids in removal of lipids and tissue fluids. Villi may contain microvilli that increase the surface area over which absorption can take place. The large intestine lack villi and instead a flat surface containing goblet cells are present.

With continued reference to FIG. 1, gut-wall includes the submucosa, which contains nerves, blood vessels, and elastic fibers containing collagen. Elastic fibers contained within the submucosa aid in stretching the gastrointestinal tract with increased capacity while also maintaining the shape of the intestine. Gut-wall includes muscular layer which contains smooth muscle that aids in peristalsis and the movement of digested material out of and along the gut. Gut-wall includes the serosa which is composed of connective tissue and coated in mucus to prevent friction damage from the intestine rubbing against other tissue. Mesenteries are also found in the serosa and suspend the intestine in the abdominal cavity to stop it from being disturbed when a person is physically active.

With continued reference to FIG. 1, gut-wall body measurement may include data describing one or more test results including results of gut-wall function, gut-wall integrity, gut-wall strength, gut-wall absorption, gut-wall permeability, intestinal absorption, gut-wall barrier function, gut-wall absorption of bacteria, gut-wall malabsorption, gut-wall gastrointestinal imbalances and the like.

With continued reference to FIG. 1, gut-wall body measurement may include any data describing blood test results of creatinine levels, lactulose levels, zonulin levels, and mannitol levels. Gut-wall body measurement may include blood test results of specific gut-wall body measurements including d-lactate, endotoxin lipopolysaccharide (LPS) Gut-wall body measurement may include data breath tests measuring lactulose, hydrogen, methane, lactose, and the like. Gut-wall body measurement may include blood test results describing blood chemistry levels of albumin, bilirubin, complete blood count, electrolytes, minerals, sodium, potassium, calcium, glucose, blood clotting factors.

With continued reference to FIG. 1, gut-wall body measurement may include one or more stool test results describing presence or absence of parasites, firmicutes, Bacteroidetes, absorption, inflammation, food sensitivities. Stool test results may describe presence, absence, and/or measurement of acetate, aerobic bacterial cultures, anerobic bacterial cultures, fecal short chain fatty acids, beta-glucuronidase, cholesterol, chymotrypsin, fecal color, *cryptosporidium* EIA, *Entamoeba histolytica*, fecal lactoferrin, *Giardia lamblia* EIA, long chain fatty acids, meat fibers and vegetable fibers, mucus, occult blood, parasite identification, phospholipids, propionate, putrefactive short chain fatty acids, total fecal fat, triglycerides, yeast culture, n-butyrate, pH and the like.

With continued reference to FIG. 1, gut-wall body measurement may include one or more stool test results describing presence, absence, and/or measurement of microorganisms including bacteria, archaea, fungi, protozoa, algae, viruses, parasites, worms, and the like. Stool test results may contain species such as *Bifidobacterium* species, *campylobacter* species, *Clostridium difficile, cryptosporidium* species, *Cyclospora cayetanensis, Cryptosporidium* EIA, *Dientamoeba fragilis, Entamoeba histolytica, Escherichia coli, Entamoeba histolytica*, Giardia, *H. pylori, Candida albicans, Lactobacillus* species, worms, macroscopic worms, mycology, protozoa, Shiga toxin *E. coli*, and the like.

With continued reference to FIG. 1, gut-wall body measurement may include one or more microscopic ova exam results, microscopic parasite exam results, protozoan polymerase chain reaction test results and the like. Gut-wall body measurement may include enzyme-linked immunosorbent assay (ELISA) test results describing immunoglobulin G (Ig G) food antibody results, immunoglobulin E (Ig E) food antibody results, Ig E mold results, IgG spice and herb results. Gut-wall body measurement may include measurements of calprotectin, eosinophil protein x (EPX), stool weight, pancreatic elastase, total urine volume, blood creatinine levels, blood lactulose levels, blood mannitol levels.

With continued reference to FIG. 1, gut-wall body measurement may include one or more elements of data describing one or more procedures examining gut including for example colonoscopy, endoscopy, large and small molecule challenge and subsequent urinary recovery using large molecules such as lactulose, polyethylene glycol-3350, and small molecules such as mannitol, L-rhamnose, polyethyleneglycol-400. Gut-wall body measurement may include data describing one or more images such as x-ray, MRI, CT scan, ultrasound, standard barium follow-through examination, barium enema, barium with contract, MRI fluoroscopy, positron emission tomography 9PET), diffusion-weighted MRI imaging, and the like.

With continued reference to FIG. 1, microbiome, as used herein, includes ecological community of commensal, symbiotic, and pathogenic microorganisms that reside on or within any of a number of human tissues and biofluids. For example, human tissues and biofluids may include the skin, mammary glands, placenta, seminal fluid, uterus, vagina, ovarian follicles, lung, saliva, oral mucosa, conjunctiva, biliary, and gastrointestinal tracts. Microbiome may include for example, bacteria, archaea, protists, fungi, and viruses. Microbiome may include commensal organisms that exist within a human being without causing harm or disease. Microbiome may include organisms that are not harmful but rather harm the human when they produce toxic metabolites such as trimethylamine. Microbiome may include pathogenic organisms that cause host damage through virulence factors such as producing toxic by-products. Microbiome may include populations of microbes such as bacteria and yeasts that may inhabit the skin and mucosal surfaces in various parts of the body. Bacteria may include for example Firmicutes species, Bacteroidetes species, Proteobacteria species, Verrumicrobia species, Actinobacteria species, Fusobacteria species, Cyanobacteria species and the like. Archaea may include methanogens such as Methanobrevibacter smithies' and Methanosphaera stadtmanae. Fungi may include *Candida* species and *Malassezia* species. Viruses may include bacteriophages. Microbiome species may vary in different locations throughout the body. For example, the genitourinary system may contain a high prevalence of *Lactobacillus* species while the gastrointestinal tract may contain a high prevalence of *Bifidobacterium* species while the lung may contain a high prevalence of *Streptococcus* and *Staphylococcus* species.

With continued reference to FIG. 1, microbiome body measurement may include one or more stool test results describing presence, absence, and/or measurement of microorganisms including bacteria, archaea, fungi, protozoa, algae, viruses, parasites, worms, and the like. Stool test results may contain species such as Ackerman's muciniphila, Anaerotruncus colihominis, bacteriology, *Bacteroides* vulgates', *Bacteroides-Prevotella*, Barnesiella species, *Bifidobacterium* longarm, *Bifidobacterium* species, Butyrivbrio crossotus, *Clostridium* species, Collinsella aerofaciens, fecal color, fecal consistency, *Coprococcus eutactus, Desulfovibrio piger, Escherichia coli, Faecalibacterium prausnitzii,* Fecal occult blood, Firmicutes to Bacteroidetes ratio, *Fusobacterium* species, *Lactobacillus* species, Methanobrevibacter *smithii*, yeast minimum inhibitory concentration, bacteria minimum inhibitory concentration, yeast mycology, fungi mycology, *Odoribacter* species, *Oxalobacter formigenes*, parasitology, *Prevotella* species, *Pseudoflavonifractor* species, *Roseburia* species, *Ruminococcus* species, *Veillonella* species and the like.

With continued reference to FIG. 1, microbiome body measurement may include one or more stool tests results that identify all microorganisms living a user's gut including bacteria, viruses, archaea, yeast, fungi, parasites, and bacteriophages. Microbiome body measurement may include DNA and RNA sequences from live microorganisms that may impact a user's health. Microbiome body measurement may include high resolution of both species and strains of all microorganisms. Microbiome body measurement may include data describing current microbe activity. Microbiome body measurement may include expression of levels of active microbial gene functions. Microbiome body measurement may include descriptions of sources of disease causing microorganisms, such as viruses found in the gastrointestinal tract such as raspberry bushy swarf virus from consuming contaminated raspberries or Pepino mosaic virus from consuming contaminated tomatoes.

With continued reference to FIG. 1, microbiome body measurement may include one or more blood test results that identify metabolites produced by microorganisms. Metabolites may include for example, indole-3-propionic acid, indole-3-lactic acid, indole-3-acetic acid, tryptophan, serotonin, kynurenine, total indoxyl sulfate, tyrosine, xanthine, 3-methylxanthine, uric acid, and the like.

With continued reference to FIG. 1, microbiome body measurement may include one or more breath test results that identify certain strains of microorganisms that may be present in certain areas of a user's body. This may include for example, lactose intolerance breath tests, methane-based breath tests, hydrogen based breath tests, fructose based breath tests. *Helicobacter pylori* breath test, fructose intolerance breath test, bacterial overgrowth syndrome breath tests and the like.

With continued reference to FIG. 1, microbiome body measurement may include one or more urinary analysis results for certain microbial strains present in urine. This may include for example, urinalysis that examines urine specific gravity, urine cytology, urine sodium, urine culture, urinary calcium, urinary hematuria, urinary glucose levels, urinary acidity, urinary protein, urinary nitrites, bilirubin, red blood cell urinalysis, and the like.

With continued reference to FIG. 1, nutrient as used herein, includes any substance required by the human body to function. Nutrients may include carbohydrates, protein, lipids, vitamins, minerals, antioxidants, fatty acids, amino acids, and the like. Nutrients may include for example vitamins such as thiamine, riboflavin, niacin, pantothenic acid, pyridoxine, biotin, folate, cobalamin, Vitamin C, Vitamin A, Vitamin D, Vitamin E, and Vitamin K. Nutrients may include for example minerals such as sodium, chloride, potassium, calcium, phosphorous, magnesium, sulfur, iron, zinc, iodine, selenium, copper, manganese, fluoride, chromium, molybdenum, nickel, aluminum, silicon, vanadium, arsenic, and boron.

With continued reference to FIG. 1, nutrients may include extracellular nutrients that are free floating in blood and exist outside of cells. Extracellular nutrients may be located in serum. Nutrients may include intracellular nutrients which may be absorbed by cells including white blood cells and red blood cells.

With continued reference to FIG. 1, nutrient body measurement may include one or more blood test results that identify extracellular and intracellular levels of nutrients. Nutrient body measurement may include blood test results that identify serum, white blood cell, and red blood cell levels of nutrients. For example, nutrient body measurement may include serum, white blood cell, and red blood cell levels of micronutrients such as Vitamin A, Vitamin B1, Vitamin B2, Vitamin B3, Vitamin B6, Vitamin B12, Vitamin B5, Vitamin C, Vitamin D, Vitamin E, Vitamin K1, Vitamin K2, and folate.

With continued reference to FIG. 1, nutrient body measurement may include one or more blood test results that identify serum, white blood cell and red blood cell levels of nutrients such as calcium, manganese, zinc, copper, chromium, iron, magnesium, copper to zinc ratio, choline, inositol, carnitine, methylmalonic acid (MMA), sodium, potassium, asparagine, glutamine, serine, coenzyme q10, cysteine, alpha lipoic acid, glutathione, selenium, eicosapentaenoic acid (EPA), docosahexaenoic acid (DHA), docosapentaenoic acid (DPA), total omega-3, lauric acid, arachidonic acid, oleic acid, total omega 6, and omega 3 index.

With continued reference to FIG. 1, nutrient body measurement may include one or more salivary test results that identify levels of nutrients including any of the nutrients as described herein. Nutrient body measurement may include hair analysis of levels of nutrients including any of the nutrients as described herein.

With continued reference to FIG. 1, genetic as used herein, includes any inherited trait. Inherited traits may include genetic material contained with DNA including for example, nucleotides. Nucleotides include adenine (A), cytosine (C), guanine (G), and thymine (T). Genetic information may be contained within the specific sequence of an individual's nucleotides and sequence throughout a gene or DNA chain. Genetics may include how a particular genetic sequence may contribute to a tendency to develop a certain disease such as cancer or Alzheimer's disease.

With continued reference to FIG. 1, genetic body measurement may include one or more results from one or more blood tests, hair tests, skin tests, urine, amniotic fluid, buccal swabs and/or tissue test to identify a user's particular sequence of nucleotides, genes, chromosomes, and/or proteins. Genetic body measurement may include tests that example genetic changes that may lead to genetic disorders. Genetic body measurement may detect genetic changes such as deletion of genetic material or pieces of chromosomes that may cause Duchenne Muscular Dystrophy. Genetic body measurement may detect genetic changes such as insertion of genetic material into DNA or a gene such as the BRCA1 gene that is associated with an increased risk of breast and ovarian cancer due to insertion of 2 extra nucleotides. Genetic body measurement may include a genetic change such as a genetic substitution from a piece of genetic material that replaces another as seen with sickle cell anemia where one nucleotide is substituted for another. Genetic body measurement may detect a genetic change such as a duplication when extra genetic material is duplicated one or more times within a person's genome such as with Charcot-Marie Tooth disease type 1. Genetic body measurement may include a genetic change such as an amplification when there is more than a normal number of copies of a gene in a cell such as HER2 amplification in cancer cells. Genetic body measurement may include a genetic change such as a chromosomal translocation when pieces of chromosomes break off and reattach to another chromosome such as with the BCR-ABL1 gene sequence that is formed when pieces of chromosome 9 and chromosome 22 break off and switch places. Genetic body measurement may include a genetic change such as an inversion when one chromosome experiences two breaks and the middle piece is flipped or inverted before reattaching. Genetic body measurement may include a repeat such as when regions of DNA contain a sequence of nucleotides that repeat a number of times such as for example in Huntington's disease or Fragile X syndrome. Genetic body measurement may include a genetic change such as a trisomy when there are three chromosomes instead of the usual pair as seen with Down syndrome with a trisomy of chromosome 21, Edwards syndrome with a trisomy at chromosome 18 or Patau syndrome with a trisomy at chromosome 13. Genetic body measurement may include a genetic change such as monosomy such as when there is an absence of a chromosome instead of a pair, such as in Turner syndrome.

With continued reference to FIG. 1, genetic body measurement may include an analysis of COMT gene that is responsible for producing enzymes that metabolize neurotransmitters. Genetic body measurement may include an analysis of DRD2 gene that produces dopamine receptors in the brain. Genetic body measurement may include an analysis of ADRA2B gene that produces receptors for noradrenaline. Genetic body measurement may include an analysis of 5-HTTLPR gene that produces receptors for serotonin. Genetic body measurement may include an analysis of BDNF gene that produces brain derived neurotrophic factor. Genetic body measurement may include an analysis of 9p21 gene that is associated with cardiovascular disease risk. Genetic body measurement may include an analysis of APOE gene that is involved in the transportation of blood lipids such as cholesterol. Genetic body measurement may include an analysis of NOS3 gene that is involved in producing enzymes involved in regulating vaso-dilation and vaso-constriction of blood vessels.

With continued reference to FIG. 1, genetic body measurement may include ACE gene that is involved in producing enzymes that regulate blood pressure. Genetic body measurement may include SLCO1B1 gene that directs pharmaceutical compounds such as statins into cells. Genetic body measurement may include FUT2 gene that produces enzymes that aid in absorption of Vitamin B12 from digestive tract. Genetic body measurement may include MTHFR gene that is responsible for producing enzymes that aid in metabolism and utilization of Vitamin B9 or folate. Genetic body measurement may include SHMT1 gene that aids in production and utilization of Vitamin B9 or folate. Genetic body measurement may include MTRR gene that produces enzymes that aid in metabolism and utilization of Vitamin B12. Genetic body measurement may include MTR gene that produces enzymes that aid in metabolism and utilization of Vitamin B12. Genetic body measurement may include FTO gene that aids in feelings of satiety or fullness after eating. Genetic body measurement may include MC4R gene that aids in producing hunger cues and hunger triggers. Genetic body measurement may include APOA2 gene that directs body to produce ApoA2 thereby affecting absorption of saturated fats. Genetic body measurement may include UCP1 gene that aids in controlling metabolic rate and thermoregulation of body. Genetic body measurement may include TCF7L2 gene that regulates insulin secretion. Genetic body measurement may include AMY1 gene that aids in digestion of starchy foods. Genetic body measurement may include MCM6 gene that controls production of lactase enzyme that aids in digesting lactose found in dairy products. Genetic body measurement may include BCMO1 gene that aids in producing enzymes that aid in metabolism and activation of Vitamin A. Genetic body measurement may include SLC23A1 gene that produce and transport Vitamin C. Genetic body measurement may include CYP2R1 gene that produce enzymes involved in production and activation of Vitamin D. Genetic body measurement may include GC gene that produce and transport Vitamin D. Genetic body measurement may include CYP1A2 gene that aid in metabolism and elimination of caffeine. Genetic body measurement may include CYP17A1 gene that produce enzymes that convert progesterone into androgens such as androstenedione, androstendiol, dehydroepiandrosterone, and testosterone.

With continued reference to FIG. 1, genetic body measurement may include CYP19A1 gene that produce enzymes that convert androgens such as androstenedione and testosterone into estrogens including estradiol and estrone.

Genetic body measurement may include SRD5A2 gene that aids in production of enzymes that convert testosterone into dihydrotestosterone. Genetic body measurement may include UFT2B17 gene that produces enzymes that metabolize testosterone and dihydrotestosterone. Genetic body measurement may include CYP1A1 gene that produces enzymes that metabolize estrogens into 2 hydroxy-estrogen. Genetic body measurement may include CYP1B1 gene that produces enzymes that metabolize estrogens into 4 hydroxy-estrogen. Genetic body measurement may include CYP3A4 gene that produces enzymes that metabolize estrogen into 16 hydroxy-estrogen. Genetic body measurement may include COMT gene that produces enzymes that metabolize 2 hydroxy-estrogen and 4 hydroxy-estrogen into methoxy estrogen. Genetic body measurement may include GSTT1 gene that produces enzymes that eliminate toxic by-products generated from metabolism of estrogens. Genetic body measurement may include GSTM1 gene that produces enzymes responsible for eliminating harmful by-products generated from metabolism of estrogens. Genetic body measurement may include GSTP1 gene that produces enzymes that eliminate harmful by-products generated from metabolism of estrogens. Genetic body measurement may include SOD2 gene that produces enzymes that eliminate oxidant by-products generated from metabolism of estrogens.

With continued reference to FIG. 1, metabolic, as used herein, includes any process that converts food and nutrition into energy. Metabolic may include biochemical processes that occur within the body. Metabolic body measurement may include blood tests, hair tests, skin tests, amniotic fluid, buccal swabs and/or tissue test to identify a user's metabolism. Metabolic body measurement may include blood tests that examine glucose levels, electrolytes, fluid balance, kidney function, and liver function. Metabolic body measurement may include blood tests that examine calcium levels, albumin, total protein, chloride levels, sodium levels, potassium levels, carbon dioxide levels, bicarbonate levels, blood urea nitrogen, creatinine, alkaline phosphatase, alanine amino transferase, aspartate amino transferase, bilirubin, and the like.

With continued reference to FIG. 1, metabolic body measurement may include one or more blood, saliva, hair, urine, skin, and/or buccal swabs that examine levels of hormones within the body such as 11-hydroxy-androstereone, 11-hydroxy-etiocholanolone, 11-keto-androsterone, 11-keto-etiocholanolone, 16 alpha-hydroxyestrone, 2-hydroxyestrone, 4-hydroxyestrone, 4-methoxyestrone, androstanediol, androsterone, creatinine, DHEA, estradiol, estriol, estrone, etiocholanolone, pregnanediol, pregnanestriol, specific gravity, testosterone, tetrahydrocortisol, tetrahydrocrotisone, tetrahydrodeoxycortisol, allo-tetrahydrocortisol.

With continued reference to FIG. 1, metabolic body measurement may include one or more metabolic rate test results such as breath tests that may analyze a user's resting metabolic rate or number of calories that a user's body burns each day rest. Metabolic body measurement may include one or more vital signs including blood pressure, breathing rate, pulse rate, temperature, and the like. Metabolic body measurement may include blood tests such as a lipid panel such as low density lipoprotein (LDL), high density lipoprotein (HDL), triglycerides, total cholesterol, ratios of lipid levels such as total cholesterol to HDL ratio, insulin sensitivity test, fasting glucose test, Hemoglobin A1C test, adipokines such as leptin and adiponectin, neuropeptides such as ghrelin, pro-inflammatory cytokines such as interleukin 6 or tumor necrosis factor alpha, anti-inflammatory cytokines such as interleukin 10, markers of antioxidant status such as oxidized low-density lipoprotein, uric acid, paraoxonase 1.

In an embodiment, and still referring to FIG. 1, computing device 104 may detect a physiological state set, defined herein as a set or more elements of physiological state data, correlated with a negative behavioral propensity and/or a problematic behavior in a behavioral training set 124, which may include training data as described above containing a plurality of pairs of physiological state sets and negative behavioral propensities and/or problematic behaviors; such a training set may be compiled using physiological state data gathered from populations of patients diagnosed with, self-reporting, and/or otherwise evincing negative behaviors, where physiological state data and/or diagnoses may be anonymized to protect patients' privacy. A pair of physiological state set and negative behavioral propensity may include, for instance, a physiological state datum or set thereof extracted from a person who was diagnosed with a particular negative behavior such as without limitation a behavioral disorder, but for whom the diagnosis may not describe a physiological cause; latent patterns may be present in such data that, when considered in larger numbers, may make correlations between combinations of physiological state datums and a given negative behavioral propensity apparent when analyzed.

Further referring to FIG. 1, in an exemplary embodiment of the above-described detection of a physiological state set correlated with a negative behavioral propensity and/or problematic behavior, computing device 104 may detect gene combinations correlated with a negative behavioral propensity and/or a problematic behavior. A "gene combination," as used in this disclosure, is a set of one or more genes; thus, as a non-limiting example, a "gene combination" that may be correlated with a disease state may include a single gene correlated with a negative behavioral propensity. As a further non-limiting example, a gene combination may include two or more genes associated with a negative behavioral propensity, including without limitation a potentially large number of genes linked to an elevated risk of a given negative behavior. Some such correlations may be unknown in medical literature, for instance where a large number of different genes in particular combinations may be linked to a given negative behavioral propensity in ways that were not anticipated by existent hypotheses for potential causes of a negative behavioral propensity and/or negative behavior. Computing device 104 may detect such novel combinations by performing one or more machine-learning algorithms as described in further detail below. Behavioral training set 124 may include a genetic training set, which may include training data as described above containing a plurality of pairs of genetic sequences and negative behavioral propensity; such a training set may be compiled using genetic sequencing gathered from populations of patients diagnosed with, self-reporting, and/or otherwise evincing negative behaviors, where genetic sequencing and/or diagnoses may be anonymized to protect patients' privacy. A pair of genetic sequence and negative behavioral propensity may include, for instance, a genetic sequence taken of a person who was diagnosed with a particular negative behavior such as without limitation a behavioral disorder, but for whom the diagnosis may not describe a genetic cause; latent patterns may be present in such data that, when considered in larger numbers, may make correlations between combinations of genes and a given negative behavioral propensity apparent when analyzed.

Still referring to FIG. 1, additional non-limiting examples of physiological state data correlated with negative behavioral propensities and/or problematic behaviors may include endocrinal measurements, such as without limitation excess or deficient dopamine correlated with disorders or other problematical behaviors relating to pleasure responses, excess or deficient testosterone correlated with problematic behaviors and/or negative behavioral propensities pertaining to desire, aggression, or other emotional responses, excess or deficient levels of cortisol correlated with eating disorders, obesity, or the like, or any other relationship between endocrinal levels and/or measurements and negative behavioral propensities and/or problematic behaviors. As a further non-limiting example, physiological state data correlated with negative behavioral propensities and/or problematic behaviors may include a correlation of one or more pathogens to negative behavioral propensities and/or problematic behaviors, such as without limitation a correlation between a toxoplasmosis infection and problematic behaviors and/or negative behavioral propensities associated with risk-seeking or otherwise reckless behavior, a correlation between streptococcal infections and pediatric autoimmune neuropsychiatric disorders associated with streptococcal infections (PANDAS), or the like. Persons skilled in the art, upon reviewing the entirety of this disclosure, will be aware of various alternative or additional forms of correlations of sets of physiological state data with negative behavioral propensities and/or problematic behaviors that are within the scope of this disclosure.

Still referring to FIG. 1, computing device 104 may generate behavior model 120 using one or more machine-learning processes. A machine learning process, also referred to as a machine-learning algorithm, is a process that automatedly uses training data and/or a training set as described above to generate an algorithm that will be performed by a computing device 104 and/or module to produce outputs given data provided as inputs; this is in contrast to a non-machine learning software program where the commands to be executed are determined in advance by a user and written in a programming language.

Continuing to refer to FIG. 1, machine-learning algorithms may be implemented using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure, Still referring to FIG. 1, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

With continued reference to FIG. 1, models may be generated using alternative or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using training data.

Still referring to FIG. 1, machine-learning algorithms may include supervised machine-learning algorithms. Supervised machine learning algorithms, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised machine-learning process may include a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data. Persons skilled in the art, upon reviewing the entirety of this disclosure, will be aware of various possible variations of supervised machine learning algorithms that may be used to determine relation between inputs and outputs.

With continued reference to FIG. 1, supervised machine-learning processes may include classification algorithms, defined as processes whereby a computing device 104 derives, from training data, a model for sorting inputs into categories or bins of data. Classification may be performed using, without limitation, linear classifiers such as without limitation logistic regression and/or naive Bayes classifiers, nearest neighbor classifiers including without limitation k-nearest neighbors classifiers, support vector machines, decision trees, boosted trees, random forest classifiers, and/or neural network-based classifiers.

Still referring to FIG. 1, machine learning processes may include unsupervised processes. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like. Unsupervised machine-learning algorithms may include, without limitation, clustering algorithms and/or cluster analysis processes, such as without limitation hierarchical clustering, centroid clustering, distribution clustering, clustering using density models, subspace models, group models, graph-based models, signed graph models, neural models, or the like. Unsupervised learning may be performed by neural networks and/or deep learning protocols as described above.

Continuing to refer to FIG. 1, machine-learning processes as described in this disclosure may be used to generate machine-learning models. A machine-learning model, as used herein, is a mathematical representation of a relationship between inputs and outputs, as generated using any machine-learning process including without limitation any process as described above, and stored in memory; an input is submitted to a machine-learning model once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model may be generated by creating an artificial neural network, such as a convolutional neural network comprising an input layer of nodes, one or more intermediate layers, and an output layer of nodes. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 1, computing device 104 may be configured to generate behavior model 120 using a first feature learning algorithm 128 and behavioral training data 124; behavioral model 120 may include without limitation a genetic model generated using genetic training data as described above. A "feature learning algorithm 128," as used herein, is a machine-learning algorithm that identifies associations between elements of data in a training data set, where particular outputs and/or inputs are not specified. For instance, and without limitation, a feature learning algorithm 128 may detect co-occurrences of sets of physiological data, as defined above, with each other and with negative behaviors and/or negative behavioral propensities. As a non-limiting example, feature learning algorithm 128 may detect co-occurrences of gene combinations, as defined above, with each other and with negative behaviors and/or negative behavioral propensities. Computing device 104 may perform a feature learning algorithm 128 by dividing physiological data from a given person into various sub-combinations of such data to create physiological data sets as described above, and evaluate which physiological data sets tend to co-occur with which other physiological data sets, negative behaviors, and/or negative behavioral propensities; for instance, where physiological state data includes genetic sequences, computing device 104 may divide each genetic sequence into individual genes and evaluate which individual genes and/or combinations thereof tend to co-occur with which other individual genes, negative behaviors, and/or negative behavioral propensities. In an embodiment, first feature learning algorithm 128 may perform clustering of data; for instance, a number of clusters into which data from training data sets may be sorted using feature learning may be set as a number of negative behavioral propensities and/or negative behaviors. In an embodiment, disease states may be placed in initialized clusters prior to a clustering algorithm being performed.

Continuing refer to FIG. 1, a feature learning and/or clustering algorithm may be implemented, as a non-limiting example, using a k-means clustering algorithm. A "k-means clustering algorithm" as used in this disclosure, includes cluster analysis that partitions n observations or unclassified cluster data entries into k clusters in which each observation or unclassified cluster data entry belongs to the cluster with the nearest mean, using, for instance behavioral training set 124 as described above. "Cluster analysis" as used in this disclosure, includes grouping a set of observations or data entries in way that observations or data entries in the same group or cluster are more similar to each other than to those in other groups or clusters. Cluster analysis may be performed by various cluster models that include connectivity models such as hierarchical clustering, centroid models such as k-means, distribution models such as multivariate normal distribution, density models such as density-based spatial clustering of applications with nose (DBSCAN) and ordering points to identify the clustering structure (OPTICS), subspace models such as biclustering, group models, graph-based models such as a clique, signed graph models, neural models, and the like. Cluster analysis may include hard clustering whereby each observation or unclassified cluster data entry belongs to a cluster or not. Cluster analysis may include soft clustering or fuzzy clustering whereby each observation or unclassified cluster data entry belongs to each cluster to a certain degree such as for example a likelihood of belonging to a cluster; for instance, and without limitation, a fuzzy clustering algorithm may be used to identify clustering of gene combinations with multiple disease states, and vice versa. Cluster analysis may include strict partitioning clustering whereby each observation or unclassified cluster data entry belongs to exactly one cluster. Cluster analysis may include strict partitioning clustering with outliers whereby observations or unclassified cluster data entries may belong to no cluster and may be considered outliers. Cluster analysis may include overlapping clustering whereby observations or unclassified cluster data entries may belong to more than one cluster. Cluster analysis may include hierarchical clustering whereby observations or unclassified cluster data entries that belong to a child cluster also belong to a parent cluster.

With continued reference to FIG. 1, computing device 104 may generate a k-means clustering algorithm receiving unclassified physiological state data and/or genetic sequence data and/or combinations thereof with negative behavioral propensities and/or negative behaviors as inputs and outputs a definite number of classified data entry cluster wherein the data entry clusters each contain cluster data entries. K-means algorithm may select a specific number of groups or clusters to output, identified by a variable "k." Generating a k-means clustering algorithm includes assigning inputs containing unclassified data to a "k-group" or "k-cluster" based on feature similarity. Centroids of k-groups or k-clusters may be utilized to generate classified data entry cluster. K-means clustering algorithm may select and/or be provided "k" variable by calculating k-means clustering algorithm for a range of k values and comparing results. K-means clustering algorithm may compare results across different values of k as the mean distance between cluster data entries and cluster centroid. K-means clustering algorithm may calculate mean distance to a centroid as a function of k value, and the location of where the rate of decrease starts to sharply shift, this may be utilized to select a k value. Centroids of k-groups or k-cluster include a collection of feature values which are utilized to classify data entry clusters containing cluster data entries. K-means clustering algorithm may act to classify a given negative behavioral propensity and/or problematic behavior to one or more genetic combinations and/or physiological data sets, enabling computing device 104 to identify gene combinations and/or physiological data sets correlated with negative behavioral propensities and/or negative behaviors.

With continued reference to FIG. 1, generating a k-means clustering algorithm may include generating initial estimates for k centroids which may be randomly generated or randomly selected from unclassified data input. K centroids may be utilized to define one or more clusters. K-means clustering algorithm may assign unclassified data to one or more k-centroids based on the squared Euclidean distance by first performing a data assigned step of unclassified data. K-means clustering algorithm may assign unclassified data to its nearest centroid based on the collection of centroids $c_i$ of centroids in set C. Unclassified data may be assigned to a cluster based on $argmin_{c_i \, \ni} dist(c_i, x)^2$, where argmin includes argument of the minimum, ci includes a collection of centroids in a set C, and dist includes standard Euclidean distance. K-means clustering module may then recompute centroids by taking mean of all cluster data entries assigned to a centroid's cluster. This may be calculated based on $ci=1/|Si|\Sigma xi \ni Si^{\ni i}$. K-means clustering algorithm may continue to repeat these calculations until a stopping criterion has been satisfied such as when cluster data entries do not change clusters, the sum of the distances have been minimized, and/or some maximum number of iterations has been reached.

Still referring to FIG. 1, k-means clustering algorithm may be configured to calculate a degree of similarity index value. A "degree of similarity index value" as used in this disclosure, includes a distance measurement indicating a measurement between each data entry cluster generated by k-means clustering algorithm and a selected physiological data set and/or combination of genes, negative behaviors and/or negative behavioral propensities. Degree of similarity index value may indicate how close a particular combination of genes, negative behaviors and/or negative behavioral propensities is to being classified by k-means algorithm to a particular cluster. K-means clustering algorithm may evaluate the distances of the combination of genes, negative behaviors and/or negative behavioral propensities to the k-number of clusters output by k-means clustering algorithm. Short distances between a combination of genes, negative behaviors and/or negative behavioral propensities and a cluster may indicate a higher degree of similarity between a combination of genes, negative behaviors and/or negative behavioral propensities and a particular cluster. Longer distances between a combination of genes, negative behaviors and/or negative behavioral propensities and a cluster may indicate a lower degree of similarity between a combination of genes and/or physiological data sets, negative behaviors and/or negative behavioral propensities and a particular cluster.

With continued reference to FIG. 1, k-means clustering algorithm selects a classified data entry cluster as a function of the degree of similarity index value. In an embodiment, k-means clustering algorithm may select a classified data entry cluster with the smallest degree of similarity index value indicating a high degree of similarity between a combination of genes and/or physiological data sets, negative behaviors and/or negative behavioral propensities and a particular data entry cluster. Alternatively or additionally k-means clustering algorithm may select a plurality of clusters having low degree of similarity index values to combination of genes and/or physiological data sets, negative behaviors and/or negative behavioral propensities, indicative of greater degrees of similarity. Degree of similarity index values may be compared to a threshold number indicating a minimal degree of relatedness suitable for inclusion of a combination of genes, negative behaviors and/or negative behavioral propensities in a cluster, where degree of similarity indices falling under the threshold number may be included as indicative of high degrees of relatedness. The above-described illustration of feature learning using k-means clustering is included for illustrative purposes only, and should not be construed as limiting potential implementation of feature learning algorithms 128; persons skilled in the art, upon reviewing the entirety of this disclosure, will be aware of various additional or alternative feature learning approaches that may be used consistently with this disclosure.

With continued reference to FIG. 1, behavioral training set 124 may be stored in and/or retrieved from one or more databases; for instance, a genetic training set may be stored in and/or retrieved from a genetic training database. Genetic training database may include any data structure suitable for use as vice database 108 as described above. Data entries in a genetic training database may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a user database may reflect categories of data consistently with this disclosure. Genetic training database may include one or more tables from which data records may be retrieved with linking data; linking data may include without limitation a genetic sequence index filed in which genetic sequence indices linking records from one or more tables to genetic sequences may be stored. As a non-limiting example, one or more tables may include a genetic sequence table listing genetic sequences with genetic sequence indices. One or more tables may include a problematic behavior table listing one or more problematic behaviors that have been associated with a given genetic sequences disease states may be linked to genetic sequences using genetic sequence indices, which may indicate collection of disease state data corresponding to a person with regard to whom a genetic sequence was extracted. One or more tables may include a negative behavior propensity table, which may link negative behavior propensities to problematic behaviors and/or genetic sequences.

Alternatively or additionally, and still referring to FIG. 1, behavioral training set 124 and/or data used therefor, including without limitation physiological state data and/or data describing negative behavioral propensities and/or problematic behaviors, may be stored in a biological marker database 132, which may be implemented in any way suitable for implementation of a vice database 116 as described above.

Figure 2:
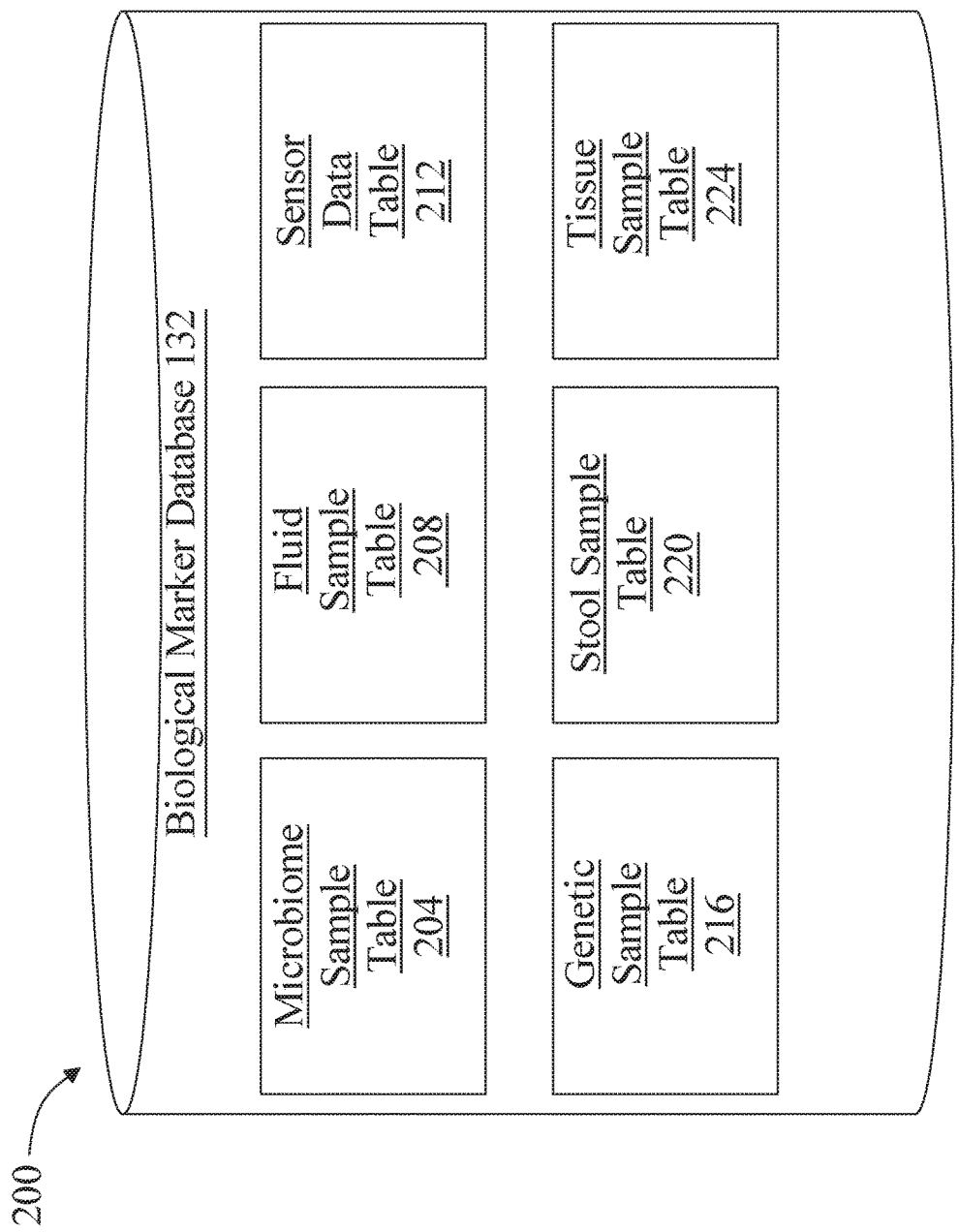
FIG. 2 is a block diagram illustrating an exemplary embodiment of a biological marker database.

Referring now to FIG. 2, an exemplary embodiment 200 of biological marker database 132 is illustrated. Biological marker database 132 may be implemented as any data structure suitable for use as clustering database 120 as described above in reference to FIG. 1. Biological marker database 132 may store one or more biological markers 112. One or more tables contained within biological marker database 132 may include microbiome sample table 204; microbiome sample table 204 may store one or more biological marker 112 relating to the microbiome. For instance and without limitation, microbiome sample table 204 may include results reflecting levels of a particular bacterial strain such as quantities of *Bifidobacterium* found in a user's gastrointestinal tract. One or more tables contained within biological marker database 132 may include fluid sample table 208; fluid sample table 208 may store one or more biological marker 112 obtained from a fluid sample. For instance and without limitation, fluid sample table 208 may include one or more entries containing results from fluids such as urine, saliva, sweat, tears, blood, mucus, cerebrospinal fluid, and the like analyzed for one or more biological marker 112. One or more tables contained within biological marker database 132 may include sensor data table 212; sensor data table 212 may include one or more biological marker 112 obtained from one or more sensors. For instance and without limitation, sensor data table 212 may include sleeping patterns of a user recorded by a sensor. One or more tables contained within biological marker database 132 may include genetic sample table 216; genetic sample table 216 may include one or more biological marker 112 containing one or more genetic sequences. For instance and without limitation, genetic sample table 216 may include a user's genetic sequence for a particular gene such as a sequence illustrating a positive breast cancer one (BRACA 1) gene. One or more tables contained within biological marker database 132 may include stool sample table 220; stool sample table 220 may include one or more biological marker 112 obtained from a stool sample. For instance and without limitation, stool sample table 220 may include a user's stool sample analyzed for the presence and/or absence of one or more parasites. One or more tables contained within biological marker database 132 may include tissue sample table 224; tissue sample table 224 may include one or more biological marker 112 obtained from one or more tissue samples. For instance and without limitation, tissue sample table 224 may include a breast tissue sample analyzed for the absence and/or presence of estrogen markers. Other tables not illustrated may include but are not limited to epigenetic, gut-wall, nutrients, and/or metabolism.

Referring again to FIG. 1, computing device 104 may be configured to receive a biological extraction 136. Biological extraction 136 may include any element and/or elements of data suitable for use as at least an element of physiological state data as described above. Biological extraction 136 may include a physically extracted sample, where a "physically extracted sample" as used in this disclosure is a sample obtained by removing and analyzing tissue and/or fluid. Physically extracted sample may include without limitation a blood sample, a tissue sample, a buccal swab, a mucous sample, a stool sample, a hair sample, a fingernail sample, or the like. Physically extracted sample may include, as a non-limiting example, at least a blood sample. As a further non-limiting example, biological extraction 136 may include at least a genetic sample. At least a genetic sample may include a complete genome of a person or any portion thereof. At least a genetic sample may include a DNA sample and/or an RNA sample. Biological extraction 136 may include an epigenetic sample, a proteomic sample, a tissue sample, a biopsy, and/or any other physically extracted sample. Biological extraction 136 may include an endocrinal sample. As a further non-limiting example, the biological extraction 136 may include a signal from at least a sensor configured to detect physiological data of a user and recording the biological extraction 136 as a function of the signal. At least a sensor may include any medical sensor and/or medical device configured to capture sensor data concerning a patient, including any scanning, radiological and/or imaging device such as without limitation x-ray equipment, computer assisted tomography (CAT) scan equipment, positron emission tomography (PET) scan equipment, any form of magnetic resonance imagery (MM) equipment, ultrasound equipment, optical scanning equipment such as photo-plethysmographic equipment, or the like. At least a sensor may include any electromagnetic sensor, including without limitation electroencephalographic sensors, magnetoencephalographic sensors, electrocardiographic sensors, electromyographic sensors, or the like. At least a sensor may include a temperature sensor. At least a sensor may include any sensor that may be included in a mobile device and/or wearable device, including without limitation a motion sensor such as an inertial measurement unit (IMU), one or more accelerometers, one or more gyroscopes, one or more magnetometers, or the like. At least a wearable and/or mobile device sensor may capture step, gait, and/or other mobility data, as well as data describing activity levels and/or physical fitness. At least a wearable and/or mobile device sensor may detect heart rate or the like. At least a sensor may detect any hematological parameter including blood oxygen level, pulse rate, heart rate, pulse rhythm, and/or blood pressure. At least a sensor may be a part of system 100 or may be a separate device in communication with system 100.

Still referring to FIG. 1, biological extraction 136 may include data describing one or more test results, including results of mobility tests, stress tests, dexterity tests, endocrinal tests, genetic tests, and/or electromyographic tests, biopsies, radiological tests, genetic tests, and/or sensory tests. Persons skilled in the art, upon reviewing the entirety of this disclosure, will be aware of various additional examples of at least a physiological sample consistent with this disclosure. At least a physiological sample may be added to physiological sample database 200.

As an illustrative example, and still referring to FIG. 1, biological extraction 136 may include a genetic sequence; a "genetic sequence," as used herein, is a series of genes identified in a nucleotide sequence of chromosomal nucleic acid of a human subject, including without limitation deoxyribonucleic acid (DNA) and/or ribonucleic acid (RNA). DNA may include chromosomal DNA, including without limitation sequences encoding particular genes as well as sequences of DNA disposed between or after gene sequences. A genetic sample may include mRNA, tRNA, or any other RNA sequence or strand. Genetic sequence may be a complete sequence of genes of the subject and/or a subset thereof.

With continued reference to FIG. 1, genetic data may be extracted from a human subject by means of a physically extracted sample. Physically extracted sample may include without limitation a tissue sample, a buccal swab, a fluid sample, a biopsy or the like. Extraction of genetic samples may be performed using any suitable physical process, including separation of nucleic acid from other tissue and/or fluid elements using, without limitation, a centrifuge. Extraction may include any form of restriction or division of a DNA and/or RNA sequence into sub-sequences, including without limitation using restriction enzymes. Extraction of genetic samples may include one or more variations of polymerase chain reaction "PCR" processes, whereby a particular strand of nucleic acid is replicated or "amplified" in a solution of nucleic acid by repeatedly exposing the solution to stimulus, such as heat, that breaks base-pair bonds, and then removing the stimulus to allow base-pair bonds to reform; as a result, a strand or sequence of nucleic acid will bond to free-floating molecules of nucleic acid, forming an inverse copy of itself, which will be separated from the strand or sequence during stimulus, and subsequently each of the strand and the inverse copy will bond to further free-floating molecules. As the above-described process is repeated, the number of copies of the strand or sequence increases exponentially. Extraction may include any suitable process to measure sequence lengths, match sequences, or the like, including without limitation electrophoresis.

Still referring to FIG. 1, received biological extraction 136, including without limitation any received genetic sequence, may be stored in any suitable manner, including without limitation in a user database 140. User database 140 may include any data structure suitable for use as vice database 116 as described above. Data entries in a user database 140 may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a user database 140 may reflect categories of data consistently with this disclosure.

Figure 3:
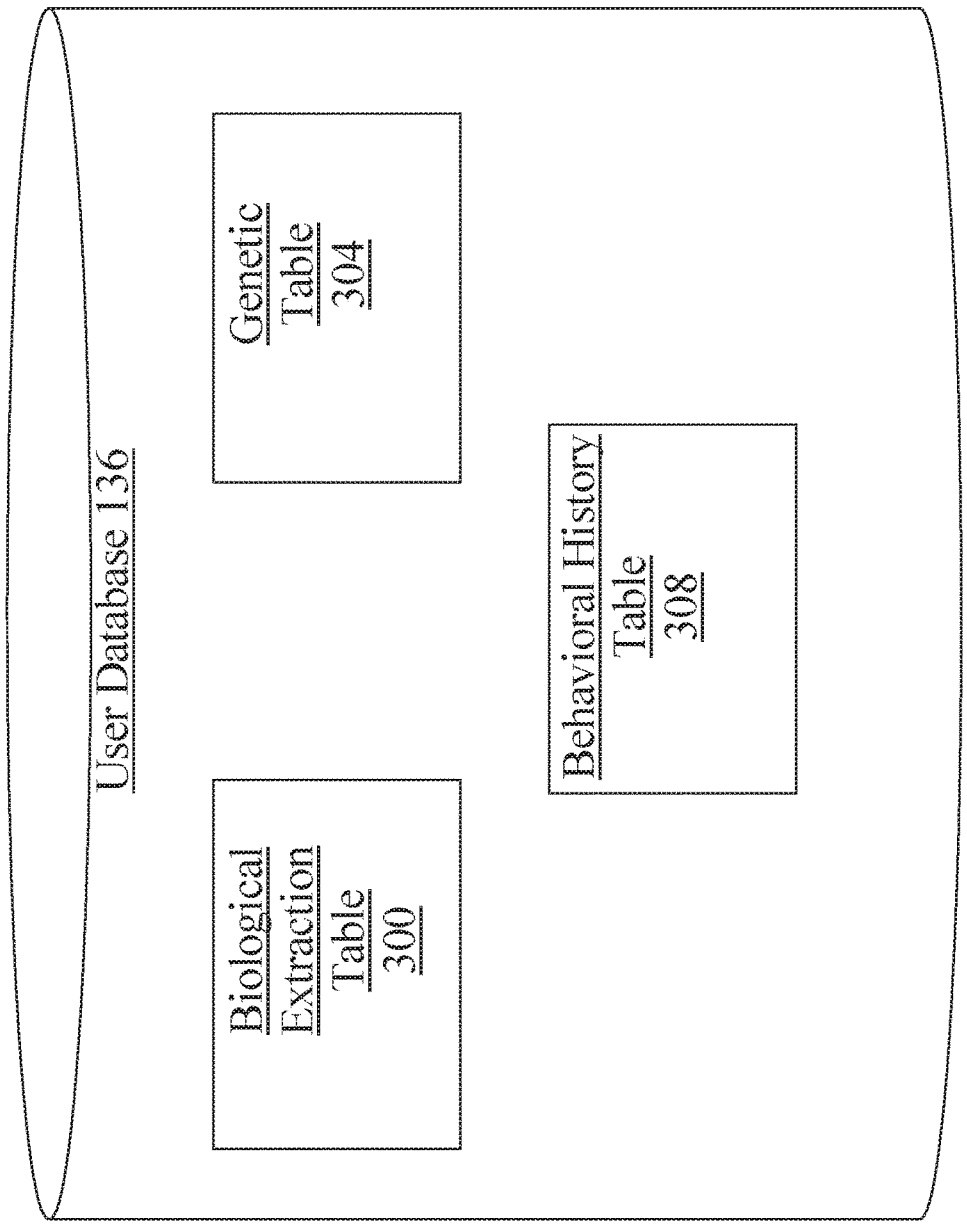
FIG. 3 is a block diagram illustrating an exemplary embodiment of a user database.

Referring now to FIG. 3, one or more tables in user database 140 may include, without limitation, a biological extraction table 300, which may be used to store biological extraction data. One or more tables in user database 140 may include, without limitation, a genetic table 304, which may be used to store genetic sequence data and/or subsequences thereof. User database 140 may include a behavioral history table 308, where current or past reports or information indicative of user behavior, including without limitation problematic behaviors, may be stored; behavioral history table 304 may store, as a non-limiting example, records of reports received from human subject and/or other persons and/or devices indicating engagement in one or more problematic behaviors as described in this disclosure. Persons skilled in the art, upon reviewing the entirety of this disclosure, will be aware of various alternative or additional data which may be stored in user database 140, including without limitation any data concerning any user activity, demographics, profile information, viewing and/or media consumption history, or the like.

Referring again to FIG. 1, computing device 104 is configured to identify, using the biological extraction 136 and the behavior model 120, a negative behavioral propensity associated with the human subject. For instance, and without limitation, computing device 104 may generate a plurality of gene combinations from genetic sequence and input such gene combinations to genetic behavior model 120; genetic behavior model 120 may identify one or more negative behavioral propensities and/or negative behaviors, which may be referred to interchangeably herein as "problematic behaviors" to which one or more gene combinations from genetic sequence are classified.

Still referring to FIG. 1, computing device 104 is configured to generate a media theme classifier 144 using thematic training data including a plurality of media items and a plurality of correlated themes. As used herein, a "media item" is an element of content transmitted over a network such as the Internet to be displayed on a user device, which may include any computing device as described in this disclosure. A media item may include, without limitation, an image, a video, an audio file, and/or a textual file. A media item may include an item of a persuasive nature, such as, without limitation, an advertisement. A media item may include a banner advertisement, a "popup" advertisement, a "pop under" advertisement, an advertisement that displays in a layer such as a layer in front of a web page, a redirect advertisement, a "splash screen" advertisement, or the like. A media item may include a "meme," a video forwarded between and/or from social media users, and/or platforms, or the like. A media item may include metadata such as owner, producer, time or place of creation, or the like A media item may include a title. A "theme" of a media item is a subject matter that the media item is promoting, describing, or otherwise providing via its content. A "principal theme" as used in this disclosure is a "main point" or primary purpose of a media item. For instance, in an advertisement, a principal theme of the advertisement may be a product, service, and/or brand being promoted or sold thereby. A principal theme of a video, story, or meme may include a main character, subject matter, place, event, or other main focus of the video, story, or meme.

Media training data 148 may be populated by receiving a plurality of user inputs, for instance via graphical user interface forms; as a non-limiting example, each such form may present to a user at least a media item and a user may select a label for each such media item from a list of labels provided to the user and/or may enter one or more words in a text entry element, which may be mapped to labels using language processing as described below; label selected by user may correspond to a user-entered identification of a principal theme of the media item. Media theme classifier 144 may input media items and output principal themes of the media items.

Continuing to refer to FIG. 1, computing device 104 is configured to generate media theme classifier 144 using a classification algorithm, which may be implemented, without limitation, using any classification algorithm suitable for generating a vice classifier 112 as described above. As a non-limiting example, media theme classifier 144 may use a K-nearest neighbors algorithm that may be configured to classify an input vector including a plurality of attributes of a media item, such as spoken or written text, objects depicted in images, metadata, etc., to clusters representing themes. Media theme classifier 144 may alternatively or additionally be created using a naïve-Bayes classification algorithm as described above. Media theme classifier 144 may enable computing device 104 to identify a single theme represented by the best-matching cluster and/or some number of best-matching clusters, such as the K best matching clusters; in the latter case, matching a theme as described below may include matching any of the K best themes, or the most probable theme may be treated as the main theme and the remaining matching clusters may be treated as identifying themes of secondary importance.

In an embodiment, and continuing to refer to FIG. 1, computing device 104 may modify media training data 148, for instance to replace a media item with plurality of objects; plurality of objects may be used as attributes of a vector associated with a media item in media training data 148, for instance for use in KNN or other classification algorithms as described above. Objects of plurality of objects may include, without limitation, objects depicted in images or frames of media, objects described in textual data extracted from images or text, and/or converted from spoken words in media, or the like. In an embodiment, computing device 104 may be configured to extract, from each media item, a plurality of content elements, such as without limitation geometric forms extracted from images and/or video frames, words or phrases of textual data, or the like. Computing device 104 may be configured to classify each content element of the plurality of content elements to an object of a plurality of objects using an object classifier 152, where the object classifier 152 may be generated using any classification algorithm as described above. Object classifier 152 may classify words, phrases, and/or geometrical forms to clusters corresponding to labels of objects, enabling a vector representing presence or relative frequency of objects to be created, for instance by populating a vector index corresponding to each of a list of objects with a number indicating presence or absence of an object corresponding to an index and/or a number indicating a number of occurrences of an object corresponding to an index. In the latter case, as a non-limiting example, a higher number may indicate a greater prevalence of a given object in the media item, which may, as a non-limiting example, cause media theme classifier 144 to classify media item to a theme consistent with a higher prevalence of a given object; prevalence and/or relative frequency of an object in media item may also be used, as described below, to determine a degree to which the object is presented in the media item for additional processing. In an embodiment, computing device 104 may replace media item with a plurality of objects as described above in media training data 148; for instance, a separate instance of media training data 148 in which media items are replaced with plurality of objects may be generated, permitting use thereof in place of the original media training data 148. Where object classifier 152 is updated, for instance by adding to a list of objects corresponding to clusters and rerunning object classifier 152 to classify to the updated list, media items stored in memory may be subjected to object classifier 152 again to update each plurality of objects; each of these actions, including without limitation rerunning object classifier 152 to classify to the updated list and/or updating plurality of objects, may be performed by computing device 104. Media theme classifier 144 may likewise be updated by rerunning classification algorithms on updated media training data 148.

Still referring to FIG. 1, object classifier 152 and/or classifiers may be run against one or more sets of object training data 156, where object training data 156 may include any form of object training data 156 as described above. Object training data 156 may include, without limitation, a plurality of data entries, each data entry including one or more content elements and one or more objects represented thereby. Object training data 156 and/or elements thereof may be entered by users, for instance via graphical user interface forms; as a non-limiting example, each such form may present to a user a geometric form, word, image, or the like, and a user may select a label for each such geometric form, word, image, or the like from a list of labels provided to the user and/or may enter one or more words in a text entry element, which may be mapped to labels using language processing as described below.

With continued reference to FIG. 1, computing device 104 may be configured to classify geometric forms identified in images and/or video frames to objects using a visual object classifier 160; that is, object classifier 152 may include a visual object classifier 160. Visual object classifier 160 may include any classifier described above; visual object classifier 160 may generate an output classifying a geometric form in a photograph to an object according to any classification algorithm as described above. In an embodiment, computing device 104 may train visual object classifier 160 using an image classification training set, which may, as a non-limiting example, include geometric forms extracted from photographs and identifications of one or more objects associated therewith. Image classification training set may, for instance, be populated by user entries of photographs, other images of objects, and/or geometric representations along with corresponding user entries identifying and/or labeling objects as described above. Computing device 104 may identify objects in the form of geometrical figures in the photographs as described above, and create training data entries in visual object classifier 160 training set with the photographs and correlated objects; in an embodiment, correlations may be further identified by matching locations of objects in a coordinate system mapped onto images to locations of geometric objects in a photograph, by receiving user identifications or "tags" of particular objects, or the like. Computing device 104 may be configured to extract the plurality of content elements by extracting a plurality of geometric forms from a visual component of the media item and classify the plurality of geometric forms using the visual object classifier 160.

Still referring to FIG. 1, computing device 104 may be configured to classify textual elements to objects using a linguistic object classifier 164; that is, object classifier 152 may include a linguistic object classifier 164. Textual elements may include words or phrases, as described in further detail below, extracted from textual data such as documents or the like. Textual elements may include other forms of data converted into textual data, such as without limitation textual data converted from audio data using speech-to-text algorithms and/or protocols, textual data extracted from images using optical character recognition (OCR), or the like. Linguistic object classifier 164 may include any classifier described above; linguistic object classifier 164 may generate an output classifying an element of textual data to an object according to any classification algorithm as described above. In an embodiment, computing device 104 may train linguistic object classifier 164 using a linguistic classification training set, which may, as a non-limiting example, include elements of textual data and identifications of one or more objects associated therewith. Linguistic classification training set may, for instance, be populated by user entries of textual data along with corresponding user entries identifying and/labeling objects as described above. Computing device 104 may be configured to extract the plurality of content elements by extracting a plurality of textual elements from a verbal component of the media item and classify the plurality of textual elements using linguistic object classifier 164.

Generation of linguistic classification training set, mapping of user entries to object labels, and/or classification of textual objects to labels may alternatively or additionally be performed using a language processing algorithm. As used herein, language processing algorithm may operate to produce a language processing model. Language processing model may include a program automatically generated by language processing algorithm to produce associations between one or more words and/or phrases, including without limitation mathematical associations, between such words. Associations between language elements, where language elements include for purposes herein extracted words and/or object labels, without limitation, mathematical associations, including without limitation statistical correlations between any language element and any other language element and/or language elements. Statistical correlations and/or mathematical associations may include probabilistic formulas or relationships indicating, for instance, a likelihood that a given word and/or phrase indicates a given object label and/or a given additional word and/or phrase. As a further example, statistical correlations and/or mathematical associations may include probabilistic formulas or relationships indicating a positive and/or negative association between at least a word and/or phrase and an object label and/or an additional word.

Still referring to FIG. 1, language processing algorithm may generate the language processing model by any suitable method, including without limitation a natural language processing classification algorithm; language processing model may include a natural language process classification model that enumerates and/or derives statistical relationships between input term and output terms. Algorithm to generate language processing model may include a stochastic gradient descent algorithm, which may include a method that iteratively optimizes an objective function, such as an objective function representing a statistical estimation of relationships between terms, including relationships between input terms and output terms, in the form of a sum of relationships to be estimated. In an alternative or additional approach, sequential tokens may be modeled as chains, serving as the observations in a Hidden Markov Model (HMM). HMMs as used herein are statistical models with inference algorithms that that may be applied to the models. In such models, a hidden state to be estimated may include an association between at least a word and/or phrase and an object label and/or an additional word. There may be a finite number of labels, words and/or phrases, and/or relationships therebetween; an HMM inference algorithm, such as the forward-backward algorithm or the Viterbi algorithm, may be used to estimate the most likely discrete state given a word or sequence of words. Language processing algorithm may combine two or more approaches. For instance, and without limitation, machine-learning program may use a combination of Naive-Bayes, Stochastic Gradient Descent (SGD), and parameter grid-searching classification techniques; the result may include a classification algorithm that returns ranked associations.

Continuing to refer to FIG. 1, generating language processing model may include generating a vector space, which may be a collection of vectors, defined as a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. Each vector in an n-dimensional vector space may be represented by an n-tuple of numerical values. Each unique extracted word and/or language element as described above may be represented by a vector of the vector space. In an embodiment, each unique extracted and/or other language element may be represented by a dimension of vector space; as a non-limiting example, each element of a vector may include a number representing an enumeration of co-occurrences of the word and/or language element represented by the vector with another word and/or language element. Vectors may be normalized, scaled according to relative frequencies of appearance and/or file sizes. In an embodiment associating language elements to one another as described above may include computing a degree of vector similarity between a vector representing each language element and a vector representing another language element; vector similarity may be measured according to any norm for proximity and/or similarity of two vectors, including without limitation cosine similarity, which measures the similarity of two vectors by evaluating the cosine of the angle between the vectors, which can be computed using a dot product of the two vectors divided by the lengths of the two vectors. Degree of similarity may include any other geometric measure of distance between vectors.

Still referring to FIG. 1, language processing algorithm may use a corpus of documents to generate associations between language elements in a language processing algorithm, and computing device 104 may then use such associations to analyze words extracted from one or more documents and determine that the one or more documents indicate a given relationship between at least a word and/or phrase and an object label and/or an additional word. In an embodiment, computing device 104 may perform this analysis using a selected set of significant documents, such as documents identified by one or more users and/or expert users, and/or a generalized body of documents and/or co-occurrence data, which may be compiled by one or more third parties. Documents and/or co-occurrence data may be received by computing device 104 by being uploaded by an expert or other persons using, without limitation, file transfer protocol (FTP) or other suitable methods for transmission and/or upload of documents; alternatively or additionally, where a document is identified by a citation, a uniform resource identifier (URI), uniform resource locator (URL) or other datum permitting unambiguous identification of the document, computing device 104 may automatically obtain the documents, co-occurrence data, or the like by downloading and/or navigating to one or more centralized and/or distributed collections thereof. Computing device 104 may alternatively or additionally receive any language processing model from one or more remote devices or third-party devices and utilize such language processing model as described above.

With continuing reference to FIG. 1, computing device 104 is configured to receive a media item 168 to be transmitted to a device operated by the human subject. Media item 168 may include any media item 168 as described above, including without limitation persuasive media items 168. Media item 168 may be scheduled for transmission to a user, as a non-limiting example, via one or more Internet and/or network-based advertising engines and/or protocols. For instance, and without limitation, a website being visited by human subject may provide advertisements such as pop-up advertisements, bann08 advertisements, redirect and/or layer-based advertisements, or the like. Alternatively or additionally, media item 168 may be scheduled for provision to user may be so scheduled in a social media feed, which may generate recommendations of media items 168 for human subject based upon past online behavior such as viewing history, searching history, history of comments and/or feedback from human subject regarding one or more items of media, or the like. As a non-limiting example, social media platforms may aggregate and/or record user network behavior choices, which may include choices made under the influence of one or more problematic behaviors, such as perusal of adult entertainment or other media tending to excite human subject's prurient interests, visits to online gambling sites, visits to sites offering packages and/or deals with regard to brick-and-mortar establishments such as casinos, liquor stores, massage parlors, gentlemen's clubs, and/or restaurants that offer products and/or services catering to one or more problematic behaviors for which human subject has a propensity or active problem as described in this disclosure.

Still referring to FIG. 1, computing device 104 may detect and/or intercept media using one or more programs and/or modules that can act to detect and/or redirect content that is being transmitted to user device; such programs and/or modules may include, without limitation, web browsers provided to a user device, "plugins" or the like operating on web browsers on a user device, programs and/or modules installed at advertisement providers, content providers, social media platforms or the like, and/or programs that route network traffic through one or more servers operated by computing device 104 as a portal for network access for human subject's device. Human subject and/or one or more third parties providing, forwarding, and/or aggregating media items 168, may agree to use, connect with, and/or install such programs and/or modules. Persons skilled in the art, upon reviewing the entirety of this disclosure, will be aware of various additional or alternative ways in which computing device 104 may receive and/or detect media items 168 within the scope of this disclosure.

With continued reference to FIG. 1, computing device 104 is configured to identify a principal theme of a received media item 168 using media theme classifier 144. Computing device 104 may input media item 168 to media theme classifier 144, which may output a principal theme, for instance by identifying a cluster, corresponding to a theme, which is most closely associated with media item 168, as described above. In an embodiment, computing device 104 may input a plurality of objects identified in media item 168 to media theme classifier 144. For instance, and without limitation, computing device 104 may extract a plurality of content elements from media item 168, where extraction may be performed in any manner described above. Computing device 104 may classifying each content element of plurality of content elements to an object of a plurality of objects using an object classifier 152, which may be any object classifier 152 or collection of object classifiers 152 as described above. Computing device 104 may input plurality of objects to the media theme classifier 144.

In an embodiment, and still referring to FIG. 1, computing device 104 is configured to determine if the principle theme matches the negative behavioral propensity; this may be performed, without limitation, by determining if principal theme matches negative behavioral propensity and/or a negative behavior for which negative behavioral propensity indicates a propensity, for instance by determining if principal theme matches a label or set of labels associated with and/or denoting negative behavior. Determination may include querying vice database 108 using principal theme; where a record is returned listing a problematic behavior and/or negative behavioral propensity matching negative behavioral propensity identified as described above, including without limitation as identified from biological extraction 136 and/or genetic sequence, computing device 104 may determine that principal theme matches negative behavioral propensity. Alternatively or additionally, and continuing to refer to FIG. 1, computing device 104 may determine if principal theme matches negative behavioral propensity and/or associated negative behavior using a vice classifier 112.

In an embodiment, and still referring to FIG. 1, computing device 104 may be further configured to determine if the principle theme matches a negative behavioral propensity of human subject by matching the principal theme to the negative behavioral propensity. In an embodiment, this determination may be accomplished by determining if a label returned from a query of vice database 108 and/or output by vice classifier 112 is identical to a label of a negative behavioral propensity and/or an associated negative behavior, and/or synonymous to such a label using, for instance, a language processing model and/or vector space as described above. If computing device 104 determines that principal theme matches a negative behavioral propensity of human subject, computing device 104 may generate a warning to be displayed on a device operated by human subject, the warning indicating that the contents of the media item 168 may be problematic and/or suggesting that the human subject should avoid consuming the media item 168. Alternatively or additionally, computing device 104 may prevent display of media item 168 on a device operated by human subject; this may, for instance be performed by activating a feature of a browser or plugin on the device operated by the human subject which prevents display of the media item 168, by deactivating a program, plugin, or other component necessary for the display, or the like. Alternatively or additionally, computing device 104 may block transmission of the media item 168 to the device. As a non-limiting example, where network communication is routed through computing device 104 to user device, blocking transmission may be accomplished by not relaying media item 168 to user device; in other embodiments, computing device 104 may transmit a message to a third party providing media that requests that the third party forgo sending the media item 168 and/or send a substitute media item 168, which may be subjected to any method steps as described above to prevent transmission of potentially problematic material.

Still referring to FIG. 1, computing device 104 may determine that principal theme does not match the negative behavioral propensity. In an embodiment, computing device 104 may permit media item 168 to be transmitted to a device operated by human subject. Alternatively or additionally, computing device 104 may be configured to extract, from the media item 168, a plurality of content elements, classify each content element of the plurality of content elements to an object of a plurality of objects using an object classifier 152, and determine that an object of the plurality of objects matches the negative behavioral propensity. Extraction of content elements may be performed, without limitation, as described above. Object classifiers 152 may be implemented as described above. In an embodiment, computing device 104 may block media item 168 upon determination that an object so classified matches negative behavioral propensity. Alternatively or additionally, computing device 104 may determine a relative frequency of an object matching negative behavioral propensity in media item 168, where relative frequency may be determined by tallying appearances of object and/or content elements associated with object, such as for instance a number of occurrences of a word associated therewith, a number of occurrences in an image of a geometric form or of geometric forms associated with the object, a number of frames of a video containing the object, or the like, resulting in a tally that is compared to a threshold number or proportion as described below; this tallying may likewise be performed for each object of a plurality of objects associated via vice database 108 and/or vice classifier 112 with a particular negative behavior and/or negative behavioral propensity. Threshold comparison may include comparison of a tally to a threshold number; alternatively or additionally threshold comparison may include tallying all objects detected in media, determining a proportion of such objects represented by an object and/or collection of objects associated with negative behavior propensity, and comparing that proportion and/or ratio to a threshold number. Tally and/or proportion may alternatively be used to grade media item 168 according to a number of appearances of object or objects associated with a negative behavioral propensity and or proportion of such appearances, where a first grade associated with a no danger of temptation may be assigned to a media item 168 containing no objects associated with negative behavioral propensity, a second grad associated with a low degree of severity of temptation for a media item 168 having a low number of occurrences and/or a low proportion of occurrences, a third grade associated with a moderate degree of severity for a media item 168 having a moderate number of occurrences and/or a moderate proportion of occurrences, a fourth grade associated with a high degree of severity of temptation for a media item 168 having a high number of occurrences and/or a high proportion of occurrences. Each grade level may result in computing device 104 performing a different response and/or requiring a different degree of combination with other factors, as described in further detail below, than each other grade level. It should be noted that the four grade levels described above are provided for exemplary purposes only; any number of grade levels may be employed, as well as differing grade levels based on absolute number or tally threshold than based on proportion thresholds. Threshold levels and/or proportions for any of the above threshold evaluations and/or gradings may be established through user inputs, based on observation and/or study of effects of media on behaviors of human subjects.

Alternatively or additionally, and continuing to refer to FIG. 1, where media theme classifier 144 identifies a most highly associated theme as a principal them, other themes having some degrees of association with media item 168, such as without limitation the remaining K-1 themes of the K nearest themes, may be referred to herein as "secondary themes." Computing device 104 may determine if a secondary theme matches a problematic behavioral propensity in any way described above for principal theme. In an embodiment, computing device 104 may block transmission and/or display of media item 168 upon determining that secondary theme matches a problematic behavioral propensity of human subject. Alternatively or additionally, computing device 104 may compare a degree of relatedness of a media item 168 with a secondary theme matching negative behavioral propensity, such as without limitation a distance in KNN from a cluster associated with the secondary theme, to a threshold, or to a plurality of thresholds associated with grades as described above. Computing device 104 may block transmission and/or display of media device for exceeding a particular threshold, matching and/or exceeding a particular grade, or the like.

Still referring to FIG. 1, computing device 104 may combine the above assessments in any suitable way that may occur to persons skilled in the art upon reviewing the entirety of this disclosure. By way of illustration, and as a non-limiting example, computing device 104 may establish a rule whereby a tally and/or proportion of one or more objects associated with negative behavior propensity, and/or grade thereof as described above, combined with a degree of relatedness and/or grade of secondary theme with negative behavioral propensity, may cause computing device 104 to block transmission and/or display of media item 168; threshold applied to object and threshold applied to secondary theme may each be insufficient to trigger blocking media item 168 alone, but the combination thereof may be sufficient to cause computing device 104 to block media item 168.

With continued reference to FIG. 1, computing device 104 may be configured to receive, receive, from a remote device, an indication that the human subject is engaging in a problematic behavior associated with negative behavioral propensity; indication may include an additional indication to an indication used to identify negative behavioral propensity as described above. Remote device may include a device operated by human subject; for instance, human subject may provide the input after a lapse in self-control. Alternatively or additionally, another person, potentially from a different remote device, may report that human subject has engaged in the problematic behavior. For instance, a family member, neighbor, spouse, boyfriend, girlfriend, ex-boyfriend, ex-girlfriend, religious leader, co-worker, or the like may observe human subject engaging in problematic behavior, such as a drinking binge, a visit to an adult entertainment institution, an excessive shopping spree, weekend at a casino, a hit of an addictive drug, or the like. Computing device 104 may track such notifications and/or compare such notifications to negative behavioral propensities. For instance, computing device 104 may record a first such report as indicative that human subject is at an elevated risk to engage in problematic behavior. In an embodiment, if computing device 104 has ever received indication that human subject engaged in problematic behavior, and human subject has a negative behavior propensity associated therewith, computing device 104 may block transmission and/or display of media in which any objects associated with negative behavior are detected and/or having a secondary theme associated with the negative behavior and/or negative behavioral propensity; computing device 104 may do this in perpetuity, or until a set period, such as 1 year, 5 years, or the like has passed since the most recent report. Alternatively or additionally, computing device 104 may set a lower threshold for exclusion of media item 168 as a result, such that, for instance, where a given threshold level of object prevalence, secondary theme relatedness, or combination thereof would have been insufficient to block transmission and/or display of media item 168, after receipt of input indicating human subject is engaging in problematic behavior, the given threshold may be sufficient to cause computing device 104 to block transmission or display. As a non-limiting example, if a grade 4 threshold as described above would trigger blocking of media item 168 absent an input indicating human subject is engaging in problematic behavior while lower grades would not, after an input indicating human subject is engaging in problematic behavior computing device 104 may block media items 168 meeting a grade 3 threshold; persons skilled in the art, upon reviewing the entirety of this disclosure, will be aware of various alternative or additional ways in which rules regarding object prevalence, degree of relatedness of secondary themes, and/or inputs indicating human subject is engaging in problematic behavior may be combined to determine whether to block transmission and/or display of media item 168.

Figure 4:
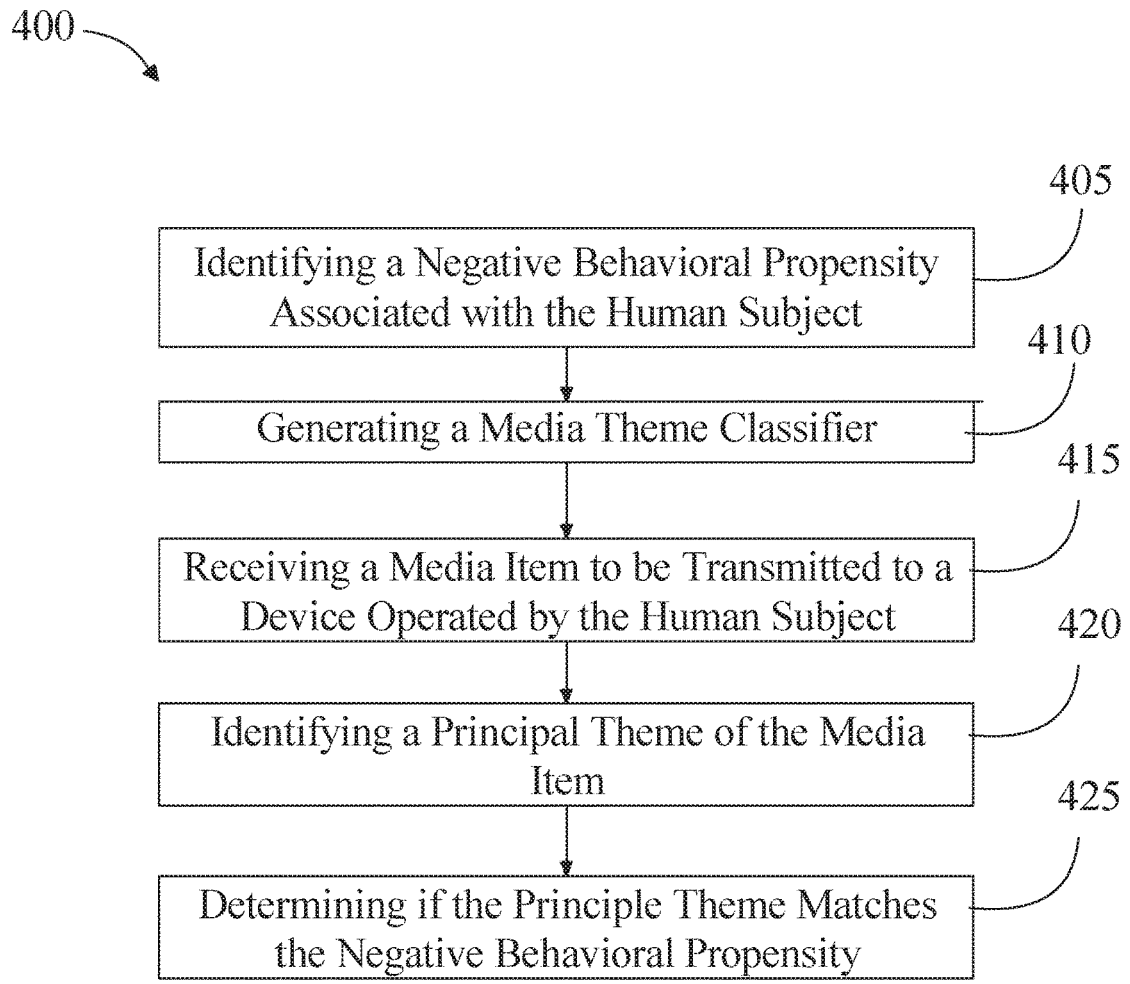
FIG. 4 is a flow diagram illustrating an exemplary embodiment of a method of classifying media according to user negative propensities.

Referring now to FIG. 4, an exemplary embodiment of a method 400 of classifying media according to user negative propensities is illustrated. At step 405, computing device 104 identifies a negative behavioral propensity associated with a human subject. This may be implemented, without limitation, as described above in reference to FIGS. 1-3. For instance, computing device may identify negative behavioral propensity by generating, using a first feature learning algorithm 128, in training data containing a plurality of pairs of genetic sequences 136 and negative behavioral propensities, a genetic behavior model 120 correlating gene combinations with negative behavioral propensities, receiving a genetic sequence, the genetic sequence including a series of genes identified in a nucleotide sequence of chromosomal nucleic acid of a human subject, and identifying using the genetic sequence and the genetic behavior model 120, a negative behavioral propensity associated with the human subject; this may be performed, without limitation as described above in reference to FIGS. 1-3. First feature learning algorithm 128 may include a k-means clustering algorithm.

Still referring to FIG. 4, at step 410, computing device 104 generates and using thematic training data including a plurality of media items 168 and a plurality of correlated themes, and using a classification algorithm, a media theme classifier 144, where the media theme classifier 144 inputs media items 168 and outputs principal themes of the media items 168; this may be performed, without limitation as described above in reference to FIGS. 1-3. Classification algorithm may include a k-nearest neighbors classification algorithm. Generating the media theme classifier 144 may include extracting, from each media item 168, a plurality of content elements, classifying each content element of the plurality of content elements to an object of a plurality of objects using an object classifier 152, and replacing the media item 168 with the plurality of objects in the thematic training data. Object classifier 152 may include a visual object classifier 160; classifying each element may include extracting the plurality of content elements by extracting a plurality of geometric forms from a visual component of the media item 168 and classifying each geometric form of the plurality of geometric forms using the visual object classifier 160. Object classifier 152 further comprises a linguistic object; classifying each element may include extracting the plurality of content elements by extracting a plurality of textual elements from a verbal component of the media item 168 and classifying each textual element of the plurality of textual elements using the linguistic object classifier 164.

At step 415, and still referring to FIG. 4, computing device 104 receives a media item 168 to be transmitted to a device operated by the human subject; this may be performed, without limitation as described above in reference to FIGS. 1-3. At step 420, computing device 104 identifies, using the media theme classifier 144, a principal theme of the media item 168; this may be performed, without limitation as described above in reference to FIGS. 1-3. For instance, and without limitation, identifying the principal theme may include extracting, from the media item 168, a plurality of content elements, classifying each content element of the plurality of content elements to an object of a plurality of objects using an object classifier 152, and inputting the plurality of objects to the media theme classifier 144.

Still referring to FIG. 4, at step 425, computing device 104 determines if the principle theme matches the negative behavioral propensity; this may be performed, without limitation as described above in reference to FIGS. 1-3. Determining if the principle theme matches the negative behavioral propensity may include matching the principal theme to the negative behavioral propensity and blocking transmission of the media item 168 to the device. Computing device 104 may extract, from the media item 168, a plurality of content elements, determine that the principal theme does not match the negative behavioral propensity, classifying each content element of the plurality of content elements to an object of a plurality of objects using an object classifier 152, and determining that an object of the plurality of objects matches the negative behavioral propensity. Computing device 104 may receive, from a remote device, an indication that the human subject is engaging in a problematic behavior associated with the negative behavioral propensity and block transmission of the media to the device operated by the human subject.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 5:
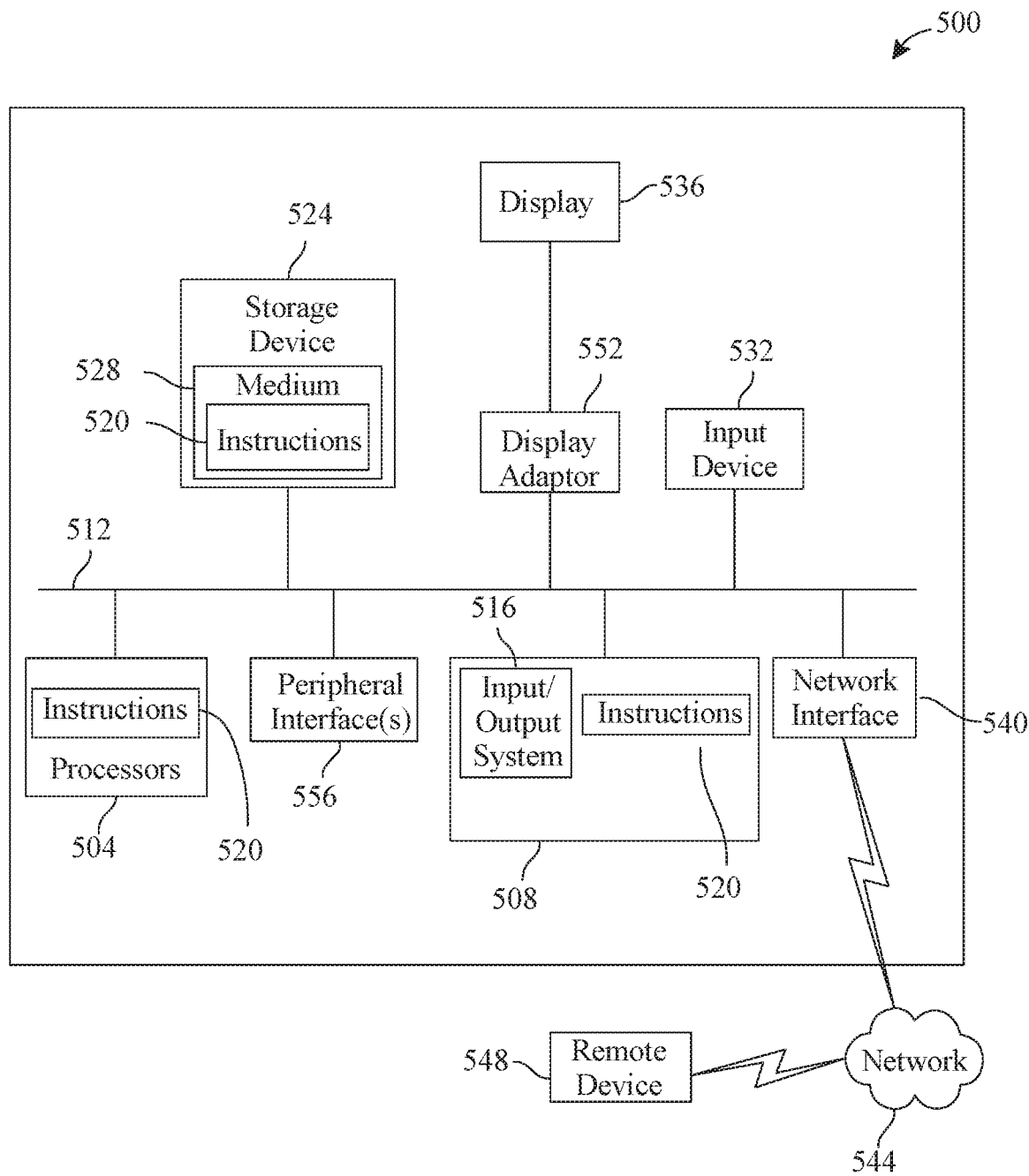
FIG. 5 is a block diagram of a computing system that can be used to implement any one or more of the methodologies disclosed herein and any one or more portions thereof.

FIG. 5 shows a diagrammatic representation of one embodiment of a computing device in the exemplary form of a computer system 500 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 500 includes a processor 504 and a memory 508 that communicate with each other, and with other components, via a bus 512. Bus 512 may include any of several types of bus structures including, but not limited to, a memory bus, a memory controller, a peripheral bus, a local bus, and any combinations thereof, using any of a variety of bus architectures.

Memory 508 may include various components (e.g., machine-readable media) including, but not limited to, a random-access memory component, a read only component, and any combinations thereof. In one example, a basic input/output system 516 (BIOS), including basic routines that help to transfer information between elements within computer system 500, such as during start-up, may be stored in memory 508. Memory 508 may also include (e.g., stored on one or more machine-readable media) instructions (e.g., software) 520 embodying any one or more of the aspects and/or methodologies of the present disclosure. In another example, memory 508 may further include any number of program modules including, but not limited to, an operating system, one or more application programs, other program modules, program data, and any combinations thereof.

Computer system 500 may also include a storage device 524. Examples of a storage device (e.g., storage device 524) include, but are not limited to, a hard disk drive, a magnetic disk drive, an optical disc drive in combination with an optical medium, a solid-state memory device, and any combinations thereof. Storage device 524 may be connected to bus 512 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 524 (or one or more components thereof) may be removably interfaced with computer system 500 (e.g., via an external port connector (not shown)). Particularly, storage device 524 and an associated machine-readable medium 528 may provide nonvolatile and/or volatile storage of machine-readable instructions, data structures, program modules, and/or other data for computer system 500. In one example, software 520 may reside, completely or partially, within machine-readable medium 528. In another example, software 520 may reside, completely or partially, within processor 504.

Computer system 500 may also include an input device 532. In one example, a user of computer system 500 may enter commands and/or other information into computer system 500 via input device 532. Examples of an input device 532 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 532 may be interfaced to bus 512 via any of a variety of interfaces (not shown) including, but not limited to, a serial interface, a parallel interface, a game port, a USB interface, a FIREWIRE interface, a direct interface to bus 512, and any combinations thereof. Input device 532 may include a touch screen interface that may be a part of or separate from display 536, discussed further below. Input device 532 may be utilized as a user selection device for selecting one or more graphical representations in a graphical interface as described above.

A user may also input commands and/or other information to computer system 500 via storage device 524 (e.g., a removable disk drive, a flash drive, etc.) and/or network interface device 540. A network interface device, such as network interface device 540, may be utilized for connecting computer system 500 to one or more of a variety of networks, such as network 544, and one or more remote devices 548 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 544, may employ a wired and/or a wireless mode of communication. In general, any network topology may be used. Information (e.g., data, software 520, etc.) may be communicated to and/or from computer system 500 via network interface device 540.

Computer system 500 may further include a video display adapter 552 for communicating a displayable image to a display device, such as display device 536. Examples of a display device include, but are not limited to, a liquid crystal display (LCD), a cathode ray tube (CRT), a plasma display, a light emitting diode (LED) display, and any combinations thereof. Display adapter 552 and display device 536 may be utilized in combination with processor 504 to provide graphical representations of aspects of the present disclosure. In addition to a display device, computer system 500 may include one or more other peripheral output devices including, but not limited to, an audio speaker, a printer, and any combinations thereof. Such peripheral output devices may be connected to bus 512 via a peripheral interface 556. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for classifying media according to user for addictive behavior, the system comprising a computing device, the computing device further configured to:
    obtain a physiological state data as a function of a physical sample;
    identify a user propensity for addictive behavior associated with a human subject as a function of the physiological state data and a behavior model, wherein the user propensity for addictive behavior identifies an addictive behavior from a predetermined plurality of addictive behaviors;
    generate, using thematic training data including a plurality of media items and a plurality of correlated items, and using a classification algorithm, a media theme classifier,
        wherein the media theme classifier inputs media items and outputs principal themes of the media item;
    receive a media item to be transmitted to a device operated by the human subject;
        identify, using the media theme classifier, a principal theme of the media item,
        wherein identifying the principal theme further comprises:
            extracting, from the media item, a plurality of media item content elements;
            classifying each content element of the plurality of media item content elements to a media item object of a plurality of media item objects using an object classifier; and
            inputting the plurality of objects to the media theme classifier; and
        determine if the principal theme matches the user propensity for addictive behavior.

2. The system of claim 1, wherein the computing device is further configured to identify the user propensity for addictive behavior by:
    generating, using a first feature learning algorithm, in training data containing a plurality of pairs of physiological data sets and propensities for addictive behavior, a behavioral model correlating physiological data sets with propensities for addictive behavior;
    receiving a biological extraction of a human subject; and
    identifying, using the biological extraction and the behavioral model, the user propensity for addictive behavior.

3. The system of claim 2, wherein the first feature learning algorithm further comprises a k-means clustering algorithm.

4. The system of claim 2, wherein the classification algorithm further comprises a k-nearest neighbors classification algorithm.

5. The system of claim 1, wherein the computing device is further configured to generate the media theme classifier by:
    extracting, from each media item, a plurality of training item content elements;
    classifying each content element of the plurality of training item content elements to a training item object of a plurality of training item objects using the object classifier; and
    replacing the media item with the plurality of training item objects in the thematic training data.

6. The system of claim 5, wherein the object classifier further comprises a visual object classifier, and the computing device is further configured to:
    extract the plurality of training item content elements by extracting a plurality of geometric forms from a visual component of the media item; and
    classify the plurality of geometric forms using the visual object classifier.

7. The system of claim 5, wherein the object classifier further comprises a linguistic object classifier, and the computing device is further configured to:
    extract the plurality of training item content elements by extracting a plurality of textual elements from a verbal component of the media item; and
    classify the plurality of textual elements using the linguistic object classifier.

8. The system of claim 1, wherein the computing device is further configured to determine if the principal theme matches the user propensity for addictive behavior by:
    matching the principal theme to the user propensity for addictive behavior; and
    blocking transmission of the media item to the device.

9. The system of claim 1, wherein the computing device is further configured to:
    extract, from the media item, a plurality of content elements;
    determine that the principal theme does not match the user propensity for addictive behavior;
    classify each content element of the plurality of content elements to an object of a plurality of objects using an object classifier; and
    determine that an object of the plurality of objects matches the user propensity for addictive behavior.

10. The system of claim 9, wherein the computing device is further configured to:
    receive, from a remote device, an indication that the human subject is engaging in a problematic behavior associated with the user propensity for addictive behavior; and
    block transmission of the media to the device operated by the human subject.

11. A method of classifying media according to user propensities for addictive behavior, the method comprising:
    obtaining, by the computing device, a physiological state data as a function of a physical sample;

identifying, by the computing device, a user propensity for addictive behavior associated with a human subject as a function of the physiological state data and a behavior model, wherein the user propensity for addictive behavior identifies an addictive behavior from a predetermined plurality of addictive behaviors;

generating, by the computing device using thematic training data including a plurality of media items and a plurality of correlated items, and using a classification algorithm, a media theme classifier, wherein the media theme classifier inputs media items and outputs principal themes of the media item;

receiving, by the computing device, a media item to be transmitted to a device operated by the human subject;

identifying, by the computing device and using the media theme classifier, a principal theme of the media item, wherein identifying the principal theme further comprises:

extracting, from the media item, a plurality of media item content elements;

classifying each content element of the plurality of media item content elements to a media item object of a plurality of media item objects using an object classifier; and inputting the plurality of objects to the media theme classifier; and determining, by the computing device, if the principal theme matches the user propensity for addictive.

12. The method of claim 11, wherein the identifying the user propensity for addictive behavior further comprises:

generating, using a first feature learning algorithm, in training data containing a plurality of pairs of genetic sequences and propensities for addictive behavior, a genetic behavioral model correlating gene combinations with propensities for addictive behavior;

receiving a genetic sequence, wherein the genetic sequence further comprises a series of genes identified in a nucleotide sequence of chromosomal nucleic acid of a human subject; and identifying, using the genetic sequence and the genetic behavioral model, the user propensity for addictive behavior.

13. The method of claim 12, wherein the first feature learning algorithm further comprises a k-means clustering algorithm.

14. The method of claim 12, wherein the classification algorithm further comprises a k-nearest neighbors classification algorithm.

15. The method of claim 11, wherein generating the media theme classifier further comprises:

extracting, from each media item, a plurality of training item content elements;

classifying each content element of the plurality of training item content elements to a training item object of a plurality of training item objects using the object classifier; and replacing the media item with the plurality of training item objects in the thematic training data.

16. The method of claim 15, wherein the object classifier further comprises a visual object classifier, and classifying each element further comprises:

extracting the plurality of training item content elements by extracting a plurality of geometric forms from a visual component of the media item; and classifying each geometric form of the plurality of geometric forms using the visual object classifier.

17. The method of claim 15, wherein the object classifier further comprises a linguistic object classifier, and classifying each element further comprises:

extracting the plurality of training item content elements by extracting a plurality of textual elements from a verbal component of the media item; and classifying each textual element of the plurality of textual elements using the linguistic object classifier.

18. The method of claim 11, wherein determining if the principal theme matches the user propensity for addictive behavior further comprises:

matching the principal theme to the user propensity for addictive behavior; and blocking transmission of the media item to the device.

19. The method of claim 11 further comprising:

extracting, from the media item, a plurality of content elements;

determining that the principal theme does not match the user propensity for addictive behavior;

classifying each content element of the plurality of content elements to an object of a plurality of objects using an object classifier; and determining that an object of the plurality of objects matches the user propensity for addictive behavior.

20. The method of claim 19 further comprising:

receiving, from a remote device, an indication that the human subject is engaging in a problematic behavior associated with the user propensity for addictive behavior; and blocking transmission of the media to the device operated by the human subject.

* * * * *